US008492384B2

(12) United States Patent
Choi et al.

(10) Patent No.: US 8,492,384 B2
(45) Date of Patent: Jul. 23, 2013

(54) IMIDAZOLYLALKYLCARBONYL DERIVATIVES AS CALCIUM CHANNEL MODULATORS AND PREPARATION METHOD THEREOF

(75) Inventors: Kyung Il Choi, Seoul (KR); Ghilsoo Nam, Nowon-gu (KR); Hye Ran Kim, Seoul (KR); Hyewhon Rhim, Seoul (KR); Seon Hee Seo, Seoul (KR); Yoon Jee Kim, Seoul (KR); Hee Sup Shin, Uiwang-si (KR); Dong Jin Kim, Seoul (KR); Ae Nim Pae, Seoul (KR); Hye Jin Chung, Seoul (KR); Yong Seo Cho, Seoul (KR); Hyunah Choo, Seoul (KR); Eun Joo Roh, Seoul (KR); Soon Bang Kang, Dohong-gu (KR); Kye Jung Shin, Seoul (KR); Hoh Gyu Hahn, Seoul (KR); Dong Yun Shin, Seoul (KR); Chan Seong Cheong, Seoul (KR); Kee Dal Nam, Seoul (KR); Yong Koo Kang, Seoul (KR); Jae Kyun Lee, Seoul (KR); Woong Seo Park, Seoul (KR); Youngsoo Kim, Yongin-si (KR); Eunice Eun-Kyeong Kim, Seoul (KR); Key-Sun Kim, Seoul (KR); Hesson Chung, Incheon (KR); Gyo Chang Keum, Seoul (KR); Cheolju Lee, Seoul (KR); Kee Hyun Choi, Guri-si (KR)

(73) Assignee: Korea Institute of Science and Technology, Seoul (KR)

( * ) Notice: Subject to any disclaimer, the term of this patent is extended or adjusted under 35 U.S.C. 154(b) by 151 days.

(21) Appl. No.: 12/492,615

(22) Filed: Jun. 26, 2009

(65) Prior Publication Data

US 2009/0325979 A1    Dec. 31, 2009

(30) Foreign Application Priority Data

Jun. 26, 2008    (KR) .................. 10-2008-0061148

(51) Int. Cl.
*A61K 31/496* (2006.01)
*C07D 233/64* (2006.01)

(52) U.S. Cl.
USPC .................... 514/254.05; 544/370; 548/341.5

(58) Field of Classification Search
None
See application file for complete search history.

(56) References Cited

U.S. PATENT DOCUMENTS

2006/0106218 A1 *    5/2006    Pennell et al. ................. 544/358

FOREIGN PATENT DOCUMENTS

| JP | 2002-128782 | | 5/2002 |
|---|---|---|---|
| KR | 10-2005-0084739 A | | 8/2005 |
| KR | 10-2006-0026315 A | | 3/2006 |
| KR | 10-6-0654328 B | | 11/2006 |
| KR | 2010119430 | * | 11/2010 |
| WO | WO 98/49149 A | | 11/1998 |
| WO | WO 2006/024160 A | | 3/2006 |
| WO | WO 2007/018319 A | | 2/2007 |

OTHER PUBLICATIONS

CA Registry No. 1017047-05-0, entered into the Registry File on Apr. 24, 2008, supplied by Ambinter Chemical Supplier.*
CA Registry No. 852916-80-4, entered into the Registry File on Jun. 24, 2005, supplied by Enamine Chemical Supplier.*
CA Registry No. 500867-39-0, entered into the Registry File on Mar. 28, 2003, supplied by Chemical Library.*
CA Registry No. 1153456-27-9, and 1153026-90-4 entered into the Registry File on Jun. 7, 2009, supplied by UkroOrgSynthesis.*
Clozel, Jean-Paul et al.: "The Structurally Novel $Ca^{2+}$ Channel Blocker Ro 40-5967, Which Binds to the [$^3$H] Desmethoxyverapamil Receptor, Is Devoid of the Negative Inotropic Effects of Verapamil in Normal and Failing Rat Hearts", *Cardiovascular Drugs and Therapy*, 4, 1990, pp. 731-736.
Dogrul, Ahmet et al.: "Reversal of experimental neuropathic pain by T-type calcium channels blockers", *Pain*, 105, 2003, pp. 159-168.
Flatters, Sarah J.L. et al.: "Ethosuximide reverses paclitaxel- and vincristine-induced painful peripheral neuropathy", *Pain*, 109, 2004, pp. 150-161.
Flatters, Sarah J.L.: "T-type calcium channels: a potential target for the treatment of chronic pain", *Drugs of the Future*, 2005, 30(6), pp. 573-580.
Fedulova, S.A. et al.: "Two Types of Calcium Channels in the Somatic Membrane of New-Born Rat Dorsal Root Ganglion Neurones", *J. Physiol.*, 1985, 359, pp. 431-446.
Yunker, Anne Marie R. et al.: "Low-Voltage-Activated ('T-Type') Calcium Channels in Review", *Journal of Bioenergetics and Biomembranes*, vol. 35, No. 6, Dec. 2003, pp. 533-575.
Jain, Kewal K.: "An evaluation of intrathecal ziconotide for the treatment of chronic pain", *Exp. Opin. Invest. Drugs*, 2000, 9(10), pp. 2403-2410.
Vanegas, Horacio et al.: "Effects of antagonists to high-threshold calcium channels upon spinal mechanisms of pain, hyperalgesia and allodynia", *Pain*, 85, 2000, pp. 9-18.
Dhosravani, Houman et al.: "Effects of $Ca_v3.2$ Channel Mutations Linked to Idiopathic Generalized Epilepsy", *Ann Neurol*, 2005, 57, pp. 745-749.
Vitko, Iuliia et al.: "Functional Characterization and Neuronal Modeling of the Effects of Childhood Absence Epilepys Variants of CACNA1H, a T-Type Calcium Channel", *The Journal of Neuroscience*, May 11, 2005, 25, 19, pp. 4844-4855.
Hefti, F. et al.: "Antihypertensive Properties of the Novel Calcium Antagonist (1S, 2S)-2-[2-[[3-(2-Benzimidazolyl)propyl] methylamino]ethyl]]-6 -fluoro-1,2,3,4 -tetrahydro-1-isopropyl-2-naphthyl Methoxyacetate Dihydrochloride in Rat Models of Hypertension", *Arzneim-Forsch./Drug Res.*, 40 (I), Nr. 4, 1990, pp. 417-421.

(Continued)

*Primary Examiner* — Emily Bernhardt
(74) *Attorney, Agent, or Firm* — Frommer Lawrence & Haug LLP; Ronald R Santucci

(57) ABSTRACT

Disclosed are novel imidazolylalkylcarbonyl derivatives useful as calcium channel modulators and a preparation method of the same. Also disclosed is a method for the treatment of diseases by administering the above compounds based on their inhibitory activity against calcium channel.

5 Claims, No Drawings

OTHER PUBLICATIONS

Moosmang, Sven et al.: "Antihypertensive Effects of the Putative T-Type Calcium Channel Antagonist Mibefradil Are Mediated by the L-Type Calcium Channel $Ca_v1.2$", *Circ Res.*, 2006, 98, pp. 105-110.

Barton, Matthew E. et al.: "The antihyperalgesic effects of the T-type calcium channel blockers ethosuximide, trimethadione, and mibefradil", *European Journal of Pharmacology*, 521, 2005, pp. 79-85.

Carbone, E. et al.: "A low-voltage-activated, fully inactivating Ca channel in vertebrate sensory neurons", *Nature*, vol. 310, Aug. 9, 1984, pp. 501-502.

Llinas, Rodolfo et al.: "Electrophysiology of Mammlian Inferior Olivary Neurones In Vitro. Different Types of Voltage-Dependent Ionic Conductances", *J. Physiol.*, 1981, 315, pp. 549-567.

Geduldig, D. et al.: "Voltage Clamp of the Aplysia Giant Neurone: Early Sodium and Calcium Currents", *J. Physiol.*, 1970, 211, pp. 217-244.

\* cited by examiner

IMIDAZOLYLALKYLCARBONYL DERIVATIVES AS CALCIUM CHANNEL MODULATORS AND PREPARATION METHOD THEREOF

CROSS-REFERENCE TO RELATED APPLICATION

This application claims the benefit under 35 U.S.C. §119 (a) of Korean Patent Application No. 10-2008-0061148, filed on Jun. 26, 2008, the entire contents of which are incorporated herein by reference.

BACKGROUND (a) Technical Field

The present invention relates to imidazolylalkylcarbonyl derivatives represented by the formula 1 effective as calcium channel modulator and method of their preparation thereof.

The present invention also relates to a method for the treatment of diseases by administering the imidazolylalkylcarbonyl derivatives based on their inhibitory activity against calcium channel.

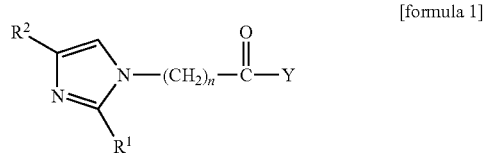

[formula 1]

In the formula 1,
Y

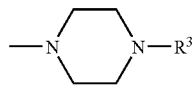

is or

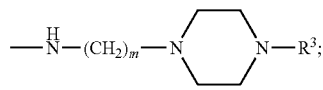

n is an integer of from 2 to 4, m is an integer of from 1 to 4; $R^1$ and $R^2$, being same or different with each other, each independently represents a hydrogen atom, $C_1$-$C_8$ alkyl group, substituted or unsubstituted phenyl group, or substituted or unsubstituted benzyl group; $R^3$ is a hydrogen atom, $C_1$-$C_8$ alkyl group, $C_1$-$C_8$ hydroxyalkyl group, CH(substituted or unsubstituted phenyl)$_2$, a heteroaromatic group having one or more hetero atom selected from O and N, substituted or unsubstituted phenyl group, or substituted or unsubstituted benzyl group; the above substituted phenyl or benzyl is respectively substituted with a substituent selected from the group consisting of halo, hydroxy, carboxy, alkoxycarbonyl, nitro, amino, mercapto, $C_1$-$C_8$ alkyl, and $C_1$-$C_8$ alkoxy groups.

(b) Background Art

The influx of calcium ions into cells through a voltage-gated calcium channels has been known to mediate numerous cellular and physiological processes including hormonal secretion, gene expression, etc. Since 1950s, the physiological importance of the influx of calcium ions through the channel proteins expressed on the cell membrane has been noticed, and calcium currents have been able to be measured under voltage-clamp conditions since 1970s (D. Gedualding, R. Gruener, J. Physiol. 1970, 211, 217-244). In 1980s, neuronal calcium channels have been classified into the two subtypes according to their voltage-dependency: high-voltage-activated (HVA) calcium channels (L-, N-, P/Q- and R-types) and low-voltage-activated (LVA) calcium channels (T-type) (R, Llinas, Y. Yarom, J. Physiol. 1981, 315, 549-567, E. Carbone, H. D. Lux, Nature, 1984, 310, 501-502, S. A. Fedulova, P. G. Kostyuk, N. S. Veselovsky, J. Physiol. 1985, 359, 431-446). While the HVA calcium channels have been named as a 'L-type' calcium channel due to their 'large' and 'long-lasting' currents, the LVA calcium channels have been named as a 'T-type' calcium channel because T-type currents are 'tiny' and 'transient.' The classification of voltage-gated calcium channels is shown below in Table 1.

TABLE 1

| Classification of calcium channel | $Ca_v$ | $\alpha_1$ subunit |
|---|---|---|
| L-type | $Ca_v1.1$ | $\alpha_{1S}$ |
| | $Ca_v1.2$ | $\alpha_{1C}$ |
| | $Ca_v1.3$ | $\alpha_{1D}$ |
| | $Ca_v1.4$ | $\alpha_{1F}$ |
| P- or Q-type | $Ca_v2.1$ | $\alpha_{1A}$ |
| N-type | $Ca_v2.2$ | $\alpha_{1B}$ |
| R-type | $Ca_v2.3$ | $\alpha_{1E}$ |
| T-type | $Ca_v3.1$ | $\alpha_{1G}$ |
| | $Ca_v3.2$ | $\alpha_{1H}$ |
| | $Ca_v3.3$ | $\alpha_{1I}$ |

As shown in Table 1, the HVA L-type calcium channels are further divided into the four subtypes, $Ca_v1.1$-$Ca_v1.4$ based on the pore-forming a1 subunit ($\alpha_{1S}$, $\alpha_{1C}$, $\alpha_{1D}$, and $\alpha_{1F}$). The HVA P/Q-, N-, and R-type calcium channels correspond to $Ca_v2.1$ ($\alpha_{1A}$), $Ca_v2.2$ ($\alpha_{1B}$), and $Ca_v2.3$ ($\alpha_{1E}$), respectively. The LVA T-type calcium channels are also further classified into the three subtypes, $Ca_v3.1$-$Ca_v3.3$ ($\alpha_{1G}$, $\alpha_{1H}$, and $\alpha_{1I}$). In vivo a1 subunits interact with other subunits such as $\alpha_2$-$\delta$, $\beta$ and $\gamma$ to form functional voltage-gated calcium channels.

Voltage-gated calcium channels have been known to be involved in neurotransmitter secretion and synaptic transmission, and expressed mainly in the central nervous system and the peripheral nervous system. Since voltage-gated calcium channels found in the neurotransmitter system are involved in pain-signal transmission, T- and N-type calcium channels are becoming a target for the development of a novel pain killer.

The pain can be divided into acute, chronic, and neuropathic pain. Among them, neuropathic pain is caused by nerve injury and lesion or dysfunction in the nerves system resulted from trauma, viral infection, drug-induced or cancer related conditions. Neuropathic pain is associated with reorganization of spinal and cortical circuits, resulting in sensitization of sensory fibers and awakening of silent nociceptors, which causes abnormal sensory phenomena such as allododynia and hyperalgesia. Because of the complexity and diversity of the pathophyological mechanisms of neuropathic pain, successful treatments remain difficult to achieve.

N- and T-type calcium channels are present in neurons, cardiac monocytes, smooth muscle and endocrinal cells. Therefore, the increase in intracellular calcium concentration would result in damage of these cells or even lead to necrosis. Since calcium channels are an endogenous modulator of calcium concentration in cells, they have been studied as a target for various drugs such as multiple neurotransmitter drugs, hormone drugs, antihypertensive drugs, anesthetic drugs, antiarrhythmic drugs, and antiepileptic drugs (A. M. Yunker, M. W. McEnery, *J. Bioenerg. Biomembranes* (2003), 35, 533).

The effectiveness of N-type calcium channels as a target for the treatment of neuropathic pain has been validated by ω-conotoxin-MVIIA, a recently approved drug and its synthetic forms, Ziconotide and SNX-III, all of which are selective blockers of N-type calcium channels (*Exp. Opin. Invest. Drugs* 9, 2403-10; Vanegas, H. and H. Schaible (2000), *Pain* 85, 9-18).

N-type calcium channels also mediate the release of neurotransmitters from the sympathetic neurons, and their antagonists can be used for the treatment of cardiac diseases such as hypertension, cardiac arrhythmia, angina pectoris, myocardial infarction and congestive heart failure.

Moreover, T-type calcium channels are involved in cell development, proliferation, epilepsy, nociception, pain, and neuropathic pain, thus becoming a target for their regulation. T-type calcium channels are present in the CNS, cardiac and vascular smooth muscles, endocrine gland of adrenal gland, sinoauricular node, and heart. T-type calcium channel blockers have been known to be effective for the treatment of cerebral diseases such as epilepsy as well as cardiac diseases such as hypertension and angina pectoris [1) Hosravani, Houman et al. "Effects of Cav3.2 channel mutations linked to idiopathic generalized epilepsy", *Annals of Neurology* (2005), 57, 745-749; 2) Vitko, Iuliia et al., "Functional characterization and neuronal modeling of the effects of childhood absence epilepsy variants of CACNA1H, a T-type calcium channel", *Journal of Neuroscience* (2005), 25 (19), 4844-4855; 3) J.-P. Clozel, et al. *Cardiovasc. Drugs Ther.* (1990), 4, 731-736; 4) Hefti, F. et al. *Arzneim.-Forsch.* (1990), 40, 417-421; 5) Moosmang, Sven et al., "Antihypertensive Effects of the Putative T-Type Calcium Channel Antagonist Mibefradil Are Mediated by the L-Type Calcium Channel Cav1. 2", *Circulation Research* (2006), 98 (1), 105-110]. Recently, it was reported that T-type calcium channel antagonists are effective for the treatment of chronic pains (*Drugs of the Future* (2005), 30, 573-580). For example, both mibefradil and ethosuximide, T-type calcium channel antagonists, have shown to inhibit mechanically and thermally evoked neuronal responses in spinal nerve ligation model of neuropathic pain in rats, thereby confirming that T-type calcium channel antagonists are effective for the treatment of neuropathic pain [1) Barton, Matthew E. et al., "The antihyperalgesic effects of the T-type calcium channel blockers ethosuximide, trimethadione, and mibefradil", *European Journal of Pharmacology* (2005), 521 (1-3), 79-85; 2) Flatters, Sarah J. L., "T-type calcium channels: A potential target for the treatment of chronic pain", *Drugs of the Future* (2005), 30 (6), 573-580; 3) Flatters, Sarah J. L. et al., "Ethosuximide reverses paclitaxel- and vincristine-induced painful peripheral neuropathy", *Pain* (2004), 109 (1-2), 150-161; 4) Dogrul, Ahmet et al., "Reversal of experimental neuropathic pain by T-type calcium channel blockers", *Pain* (2003), 105 (1-2), 159-168].

Gabapentin (Neurontin™) and Ziconotide (Prialt™) that act on N-type calcium channels are approved by FDA in the US as a drug for epilepsy and neuropathic pain treatments. However, they have a narrow therapeutic window due to the excess administration depending on the patient's characteristics, and show a side effect of sedating activity on the excess dosage. Mibefradil (Ro 40-5967, WO 98/49149), a T-type calcium channel blocker, had been used as a therapeutic treatment for hypertension and angina pectoris. However, mibefradil is metabolized by cytochrome P-450 3A4 and 2D6 with other drugs and interacts with them pharmacokinetically, which results in various side effects. As a result, mibefradil has been banned to sale so that there has been no T-type calcium channel blocker in a strict sense, and there is thus an urgent need for the development of a T-type calcium channel antagonist.

Since voltage-gated calcium channels are involved in neuronal diseases, they have been actively investigated as the major targets for the treatment of such diseases; for example, urea derivatives (WO 2006/024160) by Neuromed Technology Inc. and 3,4-dihydroquinazoline derivatives (Korea Patent No. 0610731), piperazinylalkyl isooxazole derivatives (Korea Patent No. 0616099), piperazinylalkylpyrazolyl-based derivatives (Korea Patent No. 0654328), and 3,4-dihydroquinazoline derivatives (Korea Patent No. 0610731) by big or mid-sized pharmaceutical companies.

The inventors of the present invention, after various efforts to develop a novel compound acting on voltage-gated calcium channels, have succeeded to synthesize novel imidazolylalkylcarbonyl derivatives and also found that they have an excellent antagonistic activity against T-type calcium channels, thereby completing the present invention.

SUMMARY

An object of the present invention is to provide novel imidazolylalkylcarbonyl derivatives with various substitution groups and their pharmaceutically acceptable salts.

Another object of the present invention is to provide a method of manufacturing the above novel compounds by conducting an amide-forming reaction between imidazolylalkylcarboxylic acid and a piperazine derivative. A further object of the present invention is to provide a pharmaceutical composition comprising imidazolylalkylcarbonyl derivatives and their pharmaceutically acceptable salts thereof as active ingredient for the prevention or treatment of cerebral diseases, cardiac diseases or pain-related diseases by effective blocking of calcium channel.

More specifically, the novel compounds of the present invention are useful for the prevention or treatment of diabetes; cerebral diseases such as epilepsy, Parkinson's disease, or dementia; cardiac diseases such as hypertension, cardiac arrhythmia, angina pectoris, myocardial infarction, congestive heart failure; pain-related diseases such as neuropathic pain, chronic and acute pains.

DETAILED DESCRIPTION OF INVENTION

The present invention relates to imidazolylalkylcarbonyl derivatives represented by the formula 1 or their pharmaceutically acceptable salts thereof effective for the treatment of brain diseases, heart diseases, and pain-related diseases due to their selective antagonism against T-type calcium channel.

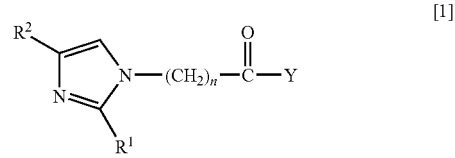

[1]

In the formula 1,
Y

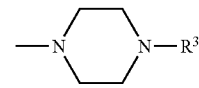

is, or

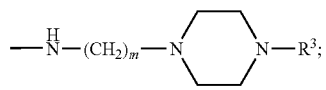

n is an integer of from 2 to 4, m is an integer of from 1 to 4; $R^1$ and $R^2$, being same or different with each other, each independently represents a hydrogen atom, $C_1$-$C_8$ alkyl group, substituted or unsubstituted phenyl group, or substituted or unsubstituted benzyl group; $R^3$ is a hydrogen atom, $C_1$-$C_8$ alkyl group, $C_1$-$C_8$ hydroxyalkyl group, CH(substituted or unsubstituted phenyl)$_2$, a heteroaromatic group having one or more hetero atom selected from O and N, substituted or unsubstituted phenyl group, or substituted or unsubstituted benzyl group; the above substituted phenyl or benzyl group is respectively substituted with a substituent selected from the group consisting of halo, hydroxy, carboxy, alkoxycarbonyl, nitro, amino, mercapto, $C_1$-$C_8$ alkyl, and $C_1$-$C_8$ alkoxy groups.

DETAILED DESCRIPTION

Hereinafter reference will now be made in detail to various embodiments of the present invention, examples of which are illustrated in the accompanying drawings, and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The imidazolylalkylcarbonyl derivatives represented by the formula 1 can have a chiral center, and these compounds usually have their racemic compounds or their isomers. Therefore, the present invention also relates to racemates, each isomer, and mixtures thereof.

Further, the present invention relates to radioactive derivatives of imidazolylalkylcarbonyl compounds represented by the formula 1. These radioactive compounds are useful for biological studies.

Further, the imidazolylalkylcarbonyl derivatives represented by the formula 1 can form pharmaceutically acceptable salts by using a conventional method in the art. For example, they can form pharmaceutically acceptable acid salts with non-toxic inorganic acids such as hydrochloric acid, bromic acid, sulfonic acid, amidosulfuric acid, phosphoric acid, nitric acid; or non-toxic organic acids such as propionic acid, succinic acid, glycolic acid, stearic acid, lactic acid, tartaric acid, citric acid, p-toluenesulfonic acid, and methanesulfonic acid.

The substitution groups of the imidazolylalkylcarbonyl derivatives represented by the formula 1 are as follows.

'Alkyl' group refers to all linear, branched and cyclic carbon chains with 1-8 carbon atoms, preferably methyl, ethyl, propyl, isopropyl, butyl, isobutyl, tert-butyl, cyclopentyl, cyclohexyl groups, etc.

'Alkoxy' group refers to alkyl groups whose carbon atoms are connected to an oxygen atom, wherein 'alkyl' is the same as defined above.

'Aryl' group refers to aromatic rings comprising 6-membered ring or bicyclic entity constructed with at least 10 atoms with resonance stabilization established, which includes phenyl, naphthyl groups, etc. The above aryl can be substituted with at least one substituent selected from the group consisting of halo, hydroxy, carboxy, alkoxycarbonyl, nitro, amino, mercapto, $C_1$-$C_8$ alkyl, $C_1$-$C_8$ alkoxy groups, etc.

'Benzyl' group refers to a reactive group where an aryl group is substituted with methylene and the methylene-substituted carbon atom can form a covalent bond with another atom.

'Heteroaromatic' group refers to stable 5-10 membered heterocyclic entities, regardless of the degree of saturation and the shape of the ring, which comprises 1-3 heteroatoms selected from N, O, and S. Examples of the heteroaromatic groups are pyridine, imidazine, pyrimidine, pyridazine, triazine, imidazole, triazole, quinoline, isoquinoline, quinazoline, quinoxaline, phthalazine, oxazole, isooxazole, thiazole, isothiazole, thiadiazole, oxadiazole, pyrrole, furan, thiophene, and their hydrogenated derivatives such as piperidine, pyrrolidine, azetidine, tetrahydrofuran and N-oxide derivatives of basic nitrogen, etc. The heteroaromatic groups may be substituted with at least one substituent selected from the group consisting of a halogen atom, alkyl, amino, alkylamino groups, etc.

In the imidazolylalkylcarbonyl derivatives represented by the formula 1, preferably, Y

is or

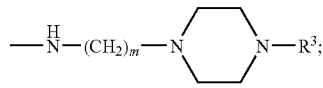

n is an integer of from 2 to 4, m is an integer of from 1 to 4; $R^1$ and $R^2$ are respectively a hydrogen atom, $C_1$-$C_8$ alkyl group, or substituted or unsubstituted phenyl group; $R^3$ is a hydrogen atom, $C_1$-$C_8$ alkyl group, $C_1$-$C_8$ hydroxyalkyl group, CH(substituted or unsubstituted phenyl)$_2$, substituted or unsubstituted phenyl group, or substituted or unsubstituted benzyl group; wherein the above substituted phenyl or benzyl is respectively substituted with 1-3 substituents selected from the group consisting of halo, $C_1$-$C_8$ alkyl and $C_1$-$C_8$ alkoxy groups.

In the imidazolylalkylcarbonyl derivatives represented by the formula 1, more preferably, Y is

or

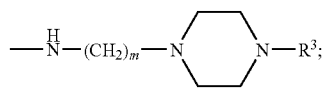

n and m respectively are an integer of 2-4; $R^1$ and $R^2$, being same or different, are respectively a hydrogen atom, methyl, ethyl, propyl, isopropyl, butyl, isobutyl, t-butyl, or phenyl group; $R^3$ is methyl, ethyl, propyl, isopropyl, butyl, isobutyl, t-butyl, phenyl, 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methylphenyl, 3-methylphenyl, 4-methylphenyl, 2,3-dimethylphenyl, 2,4-dimethylphenyl, 3,4-dimethylphenyl, 2-methoxyphenyl, 3-methoxyphenyl, 4-methoxyphenyl, 2,3-dimethoxyphenyl, 2,4-dimethoxyphenyl, 3,4-dimethoxyphenyl, benzyl, 2-fluorobenzyl, 3-fluorobenzyl, 4-fluorobenzyl, 2,3-difluorobenzyl, 2,4-difluorobenzyl, 3,4-difluorobenzyl, 2-chlorobenzyl, 3-chlorobenzyl, 4-chlorobenzyl, 2,3-dichlorobenzyl, 2,4-dichlorobenzyl, 3,4-dichlorobenzyl, 2-methylbenzyl, 3-methylbenzyl, 4-methylbenzyl, 2,3-dimethylbenzyl, 2,4-dimethylbenzyl, 3,4-dimethylbenzyl, 2-methoxybenzyl, 3-methoxybenzyl, 4-methoxybenzyl, 2,3-dimethoxybenzyl, 2,4-dimethoxybenzyl, 3,4-dimethoxybenzyl, diphenylmethyl, 2-fluorophenyl(phenyl)methyl, 3-fluorophenyl(phenyl)methyl, 4-fluorophenyl(phenyl)methyl, 2,3-difluorophenyl(phenyl)methyl, 2,4-difluorophenyl(phenyl)methyl, 3,4-difluorophenyl(phenyl)methyl, 2-chlorophenyl(phenyl)methyl, 3-chlorophenyl(phenyl)methyl, 4-chlorophenyl(phenyl)methyl, 2,3-dichlorophenyl(phenyl)methyl, 2,4-dichlorophenyl(phenyl)methyl, 3,4-dichlorophenyl(phenyl)methyl, 2-methylphenyl(phenyl)methyl, 3-methylphenyl(phenyl)methyl, 4-methylphenyl(phenyl)methyl, 2,3-dimethylphenyl(phenyl)methyl, 2,4-dimethylphenyl(phenyl)methyl, 3,4-dimethylphenyl(phenyl)methyl, 2-methoxyphenyl(phenyl)methyl, 3-methoxyphenyl(phenyl)methyl, 4-methoxyphenyl(phenyl)methyl, 2,3-dimethoxyphenyl(phenyl)methyl, 2,4-dimethoxyphenyl(phenyl)methyl, 3,4-dimethoxyphenyl(phenyl)methyl, bis(2-fluorophenyl)methyl, bis(3-fluorophenyl)methyl, bis(4-fluorophenyl)methyl, bis(2,3-difluorophenyl)methyl, bis(2,4-difluorophenyl)methyl, bis(3,4-difluorophenyl)methyl, bis(2-chlorophenyl)methyl, bis(3-chlorophenyl)methyl, bis(4-chlorophenyl)methyl, bis(2,3-dichlorophenyl)methyl, bis(2,4-dichlorophenyl)methyl, bis(3,4-dichlorophenyl)methyl, bis(2-methylphenyl)methyl, bis(3-methylphenyl)methyl, bis(4-methylphenyl)methyl, bis(2,3-dimethylphenyl)methyl, bis(2,4-dimethylphenyl)methyl, bis(3,4-dimethylphenyl)methyl, bis(2-methoxyphenyl)methyl, bis(3-methoxyphenyl)methyl, bis(4-methoxyphenyl)methyl, bis(2,3-dimethoxyphenyl)methyl, bis(2,4-dimethoxyphenyl)methyl, or bis(3,4-dimethoxyphenyl)methyl group.

The examples of the compounds represented by the formula 1 according to the present invention are as follows:

1-N-(4-diphenylmethylpiperazin-1-yl)carbonylethyl-4-phenylimidazole [Compound No. 1]
1-N-(4-benzylpiperazin-1-yl)carbonylethyl-4-phenylimidazole [Compound No. 2]
1-N-[4-(2,3-dimethylphenyl)piperazin-1-yl]carbonylethyl-4-phenylimidazole [Compound No. 3]
1-N-[4-(2,4-dimethylphenyl)piperazin-1-yl]carbonylethyl-4-phenylimidazole [Compound No. 4]
1-N-[4-(4-chlorobenzyl)piperazin-1-yl]carbonylethyl-4-phenylimidazole [Compound No. 5]
1-N-[4-(4-chlorophenyl) (phenyl)methylpiperazin-1-yl]carbonylethyl-4-phenylimidazole [Compound No. 6]
1-N-[4-(4-fluorobenzyl)piperazin-1-yl]carbonylethyl-4-phenylimidazole [Compound No. 7]
1-N-[4-(3,4-dichlorobenzyl)piperazin-1-yl]carbonylethyl-4-phenylimidazole [Compound No. 8]
1-N-(4-ethylpiperazin-1-yl)carbonylethyl-4-phenylimidazole [Compound No. 9]
1-N-(4-methylpiperazin-1-yl)carbonylethyl-4-phenylimidazole [Compound No. 10]
1-N-[4-(2-hydroxyethyl)piperazin-1-yl]carbonylethyl-4-phenylimidazole [Compound No. 11]
1-N-(4-benzylpiperazin-1-yl)carbonylethyl-2-phenylimidazole [Compound No. 12]
1-N-(4-diphenylmethylpiperazin-1-yl)carbonylethyl-2-phenylimidazole [Compound No. 13]
1-N-[4-(2-fluorophenyl)piperazin-1-yl]carbonylethyl-2-phenylimidazole [Compound No. 14]
1-N-[4-(2,3-dimethylphenyl)piperazin-1-yl]carbonylethyl-2-phenylimidazole [Compound No. 15]
1-N-[4-(2,4-dimethylphenyl)piperazin-1-yl]carbonylethyl-2-phenylimidazole [Compound No. 16]
1-N-[4-(4-chlorobenzyl)piperazin-1-yl]carbonylethyl-2-phenylimidazole [Compound No. 17]
1-N-[4-(3,4-dichlorobenzyl)piperazin-1-yl]carbonylethyl-2-phenylimidazole [Compound No. 18]
1-N-[4-(4-chlorophenyl)(phenyl)methylpiperazin-1-yl]carbonylethyl-2-phenylimidazole [Compound No. 19]
1-N-[4-(2-fluorophenyl)piperazin-1-yl]carbonylethyl-4-phenylimidazole [Compound No. 20]
1-N-[4-(4-fluorobenzyl)piperazin-1-yl]carbonylethyl-2-phenylimidazole [Compound No. 21]
1-N-(4-methylpiperazin-1-yl)carbonylethyl-2-phenylimidazole [Compound No. 22]
1-N-(4-ethylpiperazin-1-yl)carbonylethyl-2-phenylimidazole [Compound No. 23]
1-N-[4-(2-hydroxyethyl)piperazin-1-yl]carbonylethyl-2-phenylimidazole [Compound No. 24]
1-N-[4-(3-chlorophenyl)piperazin-1-yl]carbonylethyl-4-phenylimidazole [Compound No. 25]
1-N-[4-(3-chlorophenyl)piperazin-1-yl]carbonylethyl-2-phenylimidazole [Compound No. 26]
1-N-[4-(4-methoxyphenyl)piperazin-1-yl]carbonylethyl-4-phenylimidazole [Compound No. 27]
1-N-[4-(4-methoxyphenyl)piperazin-1-yl]carbonylethyl-2-phenylimidazole [Compound No. 28]
1-N-(4-phenylpiperazin-1-yl)carbonylethyl-4-methylimidazole [Compound No. 29]
1-N-(4-diphenylmethylpiperazin-1-yl)carbonylethyl-4-methylimidazole 9 [Compound No. 30]
1-N-(4-benzylpiperazin-1-yl)carbonylethyl-4-methylimidazole [Compound No. 31]
1-N-[4-(2,3-dimethylphenyl)piperazin-1-yl]carbonylethyl-4-methylimidazole [Compound No. 32]
1-N-(4-benzylpiperazin-1-yl)carbonylethyl-2-methylimidazole [Compound No. 33]
1-N-(4-phenylpiperazin-1-yl)carbonylethyl-2-methylimidazole [Compound No. 34]
1-N-(4-diphenylmethylpiperazin-1-yl)carbonylethyl-2-methylimidazole [Compound No. 35]
1-N-[4-(2,3-dimethylphenyl)piperazin-1-yl]carbonylethyl-2-methylimidazole [Compound No. 36]
1-N-[4-(2,4-dimethylphenyl)piperazin-1-yl]carbonylethyl-2-methylimidazole [Compound No. 37]
1-N-[4-(2,4-dimethylphenyl)piperazin-1-yl]carbonylethyl-4-methylimidazole [Compound No. 38]
1-N-[4-(2-fluorophenyl)piperazin-1-yl]carbonylethyl-2-methylimidazole [Compound No. 39]
1-N-[4-(2-fluorophenyl)piperazin-1-yl]carbonylethyl-4-methylimidazole [Compound No. 40]
1-N-[4-(4-chlorobenzyl)piperazin-1-yl]carbonylethyl-2-methylimidazole [Compound No. 41]
1-N-[4-(4-chlorobenzyl)piperazin-1-yl]carbonylethyl-4-methylimidazole [Compound No. 42]

1-N-[4-(4-fluorobenzyl)piperazin-1-yl]carbonylethyl-2-methylimidazole [Compound No. 43]
1-N-[4-(4-fluorobenzyl)piperazin-1-yl]carbonylethyl-4-methylimidazole [Compound No. 44]
1-N-[4-(4-chlorophenyl)(phenyl)methylpiperazin-1-yl]carbonylethyl-4-methylimidazole [Compound No. 45]
1-N-[4-(4-chlorophenyl)(phenyl)methylpiperazin-1-yl]carbonylethyl-2-methylimidazole [Compound No. 46]
1-N-[4-(3,4-dichlorobenzyl)piperazin-1-yl]carbonylethyl-2-methylimidazole [Compound No. 47]
1-N-[4-(3,4-dichlorobenzyl)piperazin-1-yl]carbonylethyl-4-methylimidazole [Compound No. 48]
1-N-[4-(3-chlorophenyl)piperazin-1-yl]carbonylethyl-2-methylimidazole [Compound No. 49]
1-N-[4-(3-chlorophenyl)piperazin-1-yl]carbonylethyl-4-methylimidazole [Compound No. 50]
1-N-[4-(4-methoxyphenyl)piperazin-1-yl]carbonylethyl-2-methylimidazole [Compound No. 51]
1-N-[4-(4-methoxyphenyl)piperazin-1-yl]carbonylethyl-4-methylimidazole [Compound No. 52]
1-N-(4-phenylpiperazin-1-yl)carbonylethyl-4-phenylimidazole [Compound No. 53]
1-N-(4-phenylpiperazin-1-yl)carbonylethyl-2-phenylimidazole [Compound No. 54]
1-N-[2-(4-diphenylmethylpiperazin-1-yl)ethyl]carbamoylethyl-4-phenylimidazole [Compound No. 55]
1-N-{2-[4-(2,3-dimethylphenyl)(phenyl)methylpiperazin-1-yl]ethyl}carbamoylethyl-4-phenylimidazole [Compound No. 56]
1-N-{2-[4-(3-chlorobenzyl)piperazin-1-yl]ethyl}carbamoylethyl-4-phenylimidazole [Compound No. 57]
1-N-{2-[4-(3,4-dichlorobenzyl)piperazin-1-yl]ethyl}carbamoylethyl-4-phenylimidazole [Compound No. 58]
1-N-{2-[4-(3,4-dichlorobenzyl)piperazin-1-yl]ethyl}carbamoylethyl-2-phenylimidazole [Compound No. 59]
1-N-{2-[4-(3-chlorobenzyl)piperazin-1-yl]ethyl}carbamoylethyl-2-phenylimidazole [Compound No. 60]
1-N-{2-[4-(2,4-dimethylphenyl)piperazin-1-yl]ethyl}carbamoylethyl-4-phenylimidazole [Compound No. 61]
1-N-{2-[4-(2,4-dimethylphenyl)piperazin-1-yl]ethyl}carbamoylethyl-2-phenylimidazole [Compound No. 62]
1-N-{2-[4-(4-chlorophenyl) (phenyl)methylpiperazin-1-yl]ethyl}carbamoylethyl-2-phenylimidazole [Compound No. 63]
1-N-{2-[4-(4-chlorophenyl) (phenyl)methylpiperazin-1-yl]ethyl}carbamoylethyl-4-phenylimidazole [Compound No. 64]
1-N-{2-[4-(2-fluorobenzyl)piperazin-1-yl]ethyl}carbamoylethyl-2-phenylimidazole [Compound No. 65]
1-N-{2-[4-(2-fluorobenzyl)piperazin-1-yl]ethyl}carbamoylethyl-4-phenylimidazole [Compound No. 66]
1-N-{2-[4-(3-methylbenzyl)piperazin-1-yl]ethyl}carbamoylethyl-4-phenylimidazole 의 [Compound No. 67]
1-N-{2-[4-(3-methylbenzyl)piperazin-1-yl]ethyl}carbamoylethyl-2-phenylimidazole [Compound No. 68]
1-N-{2-[4-(4-fluorobenzyl)piperazin-1-yl]ethyl}carbamoylethyl-2-phenylimidazole [Compound No. 69]
1-N-{2-[4-(4-fluorobenzyl)piperazin-1-yl]ethyl}carbamoylethyl-4-phenylimidazole [Compound No. 70]
1-N-[2-(4-phenylpiperazin-1-yl)ethyl]carbamoylethyl-4-phenylimidazole [Compound No. 71]
1-N-[2-(4-phenylpiperazin-1-yl)ethyl]carbamoylethyl-2-phenylimidazole [Compound No. 72]
1-N-{2-[4-(4-fluorophenyl)piperazin-1-yl]ethyl}carbamoylethyl-4-phenylimidazole [Compound No. 73]
1-N-{2-[4-(4-fluorophenyl)piperazin-1-yl]ethyl}carbamoylethyl-2-phenylimidazole [Compound No. 74]
1-N-{2-[4-(4-methoxyphenyl)piperazin-1-yl]ethyl}carbamoylethyl-4-phenylimidazole [Compound No. 75]
1-N-{2-[4-(4-methoxyphenyl)piperazin-1-yl]ethyl}carbamoylethyl-2-phenylimidazole [Compound No. 76]
1-N-{2-[4-(2-fluorophenyl)piperazin-1-yl]ethyl}carbamoylethyl-4-phenylimidazole [Compound No. 77]
1-N-{2-[4-(2-fluorophenyl)piperazin-1-yl]ethyl}carbamoylethyl-2-phenylimidazole [Compound No. 78]
1-N-{2-[4-(3-chlorophenyl)piperazin-1-yl]ethyl}carbamoylethyl-4-phenylimidazole [Compound No. 79]
1-N-{2-[4-(3-chlorophenyl)piperazin-1-yl]ethyl}carbamoylethyl-2-phenylimidazole [Compound No. 80]
1-N-{2-[4-(2,3-dimethylphenyl)piperazin-1-yl]ethyl}carbamoylethyl-2-phenylimidazole [Compound No. 81]
1-N-[2-(4-diphenylmethylpiperazin-1-yl)ethyl]carbamoylethyl-4-phenylimidazole [Compound No. 82]
1-N-[2-(4-benzylpiperazin-1-yl)ethyl]carbamoylethyl-2-phenylimidazole [Compound No. 83]
1-N-[2-(4-benzylpiperazin-1-yl)ethyl]carbamoylethyl-4-phenylimidazole [Compound No. 84]
1-N-[2-(4-phenylpiperazin-1-yl)ethyl]carbamoylethyl-2-methylimidazole [Compound No. 85]
1-N-[2-(4-phenylpiperazin-1-yl)ethyl]carbamoylethyl-4-methylimidazole [Compound No. 86]
1-N-{2-[4-(4-fluorophenyl)piperazin-1-yl]ethyl}carbamoylethyl-4-methylimidazole [Compound No. 87]
1-N-{2-[4-(4-fluorophenyl)piperazin-1-yl]ethyl}carbamoylethyl-2-methylimidazole [Compound No. 88]
1-N-{2-[4-(4-fluorobenzyl)piperazin-1-yl]ethyl}carbamoylethyl-2-methylimidazole [Compound No. 89]
1-N-{2-[4-(4-fluorobenzyl)piperazin-1-yl]ethyl}carbamoylethyl-4-methylimidazole [Compound No. 90]
1-N-{2-[4-(2-fluorophenyl)piperazin-1-yl]ethyl}carbamoylethyl-2-methylimidazole [Compound No. 91]
1-N-{2-[4-(2-fluorophenyl)piperazin-1-yl]ethyl}carbamoylethyl-4-methylimidazole [Compound No. 92]

1-N-{2-[4-(4-chlorophenyl) (phenyl)methylpiperazin-1-yl]
ethyl}carbamoylethyl-2-methylimidazole [Compound No. 93]
1-N-{2-[4-(4-chlorophenyl) (phenyl)methylpiperazin-1-yl]
ethyl}carbamoylethyl-4-methylimidazole [Compound No. 94]
1-N-{2-[4-benzylpiperazin-1-yl]ethyl}carbamoylethyl-4-methylimidazole [Compound No. 95]
1-N-[2-(4-diphenylmethylpiperazin-1-yl)ethyl]carbamoylethyl-2-methylimidazole [Compound No. 96]
1-N-{2-[4-(4-methoxybenzyl)piperazin-1-yl]
ethyl}carbamoylethyl-4-methylimidazole [Compound No. 97]
1-N-{2-[4-(4-methoxybenzyl)piperazin-1-yl]
ethyl}carbamoylethyl-2-methylimidazole [Compound No. 98]
1-N-{2-[4-(3,4-dichlorobenzyl)piperazin-1-yl]
ethyl}carbamoylethyl-2-methylimidazole [Compound No. 99]
1-N-{2-[4-(3,4-dichlorobenzyl)piperazin-1-yl]
ethyl}carbamoylethyl-4-methylimidazole [Compound No. 100]
1-N-{2-[4-(4-chlorobenzyl)piperazin-1-yl]
ethyl}carbamoylethyl-2-methylimidazole [Compound No. 101]
1-N-{2-[4-(4-chlorobenzyl)piperazin-1-yl]
ethyl}carbamoylethyl-4-methylimidazole [Compound No. 102]
1-N-{2-[4-(3-chlorophenyl)piperazin-1-yl]
ethyl}carbamoylethyl-2-methylimidazole [Compound No. 103]
1-N-{2-[4-(3-chlorophenyl)piperazin-1-yl]
ethyl}carbamoylethyl-4-methylimidazole [Compound No. 104]
1-N-{2-[4-diphenylmethylpiperazin-1-yl]
ethyl}carbamoylethyl-4-methylimidazole [Compound No. 105].

The present invention also relates to a method of manufacturing imidazolylalkylcarbonyl derivatives as shown in the Reaction Scheme 1 below. In the Reaction Scheme 1, imidazolylalkylcarboxylic acid represented by the formula 2 is reacted with a piperazine derivative represented by the formula 3 in the presence of a suitable coupling agent to form an amide linkage thereby obtaining a compound represented by the formula 1.

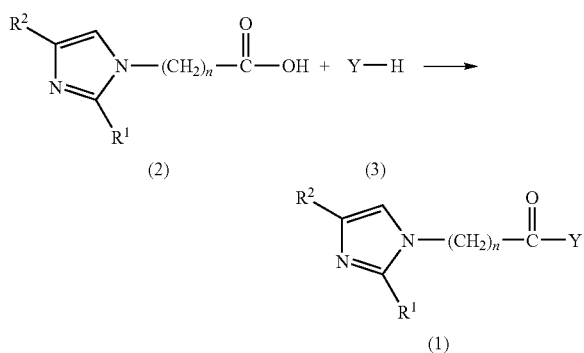

In the above Reaction Scheme 1, Y, $R^1$, $R^2$, $R^3$ and n are the same as defined above.

The amide linkage forming agents can be selected from various coupling agents developed recently in the field of organic synthesis (S.-Y. Han, Y.-A. Kim), *Tetrahedron* 60, 2004, 2447-2467). More specifically, phosphonium-, ammonium-, carbodiimide-, imidazolinium- or organic phosphine-based reagents can be used.

Examples of the reaction solvent to be used in the above reaction are $C_{1-6}$ low alcohols such as methanol, ethanol, and propanol, tetrahydrofuran, and halogenated solvents such as chloroform and methylene chloride.

The reaction can be performed in the range of −30° C. to reflux temperature of the solvent, preferably at 10° C.-25° C., more preferably at room temperature.

Imidazolylalkylcarboxylic acid, a reactant used in the method according to the present invention as represented by the above formula 2, can be manufactured by a method shown in the Reaction Scheme 2 below.

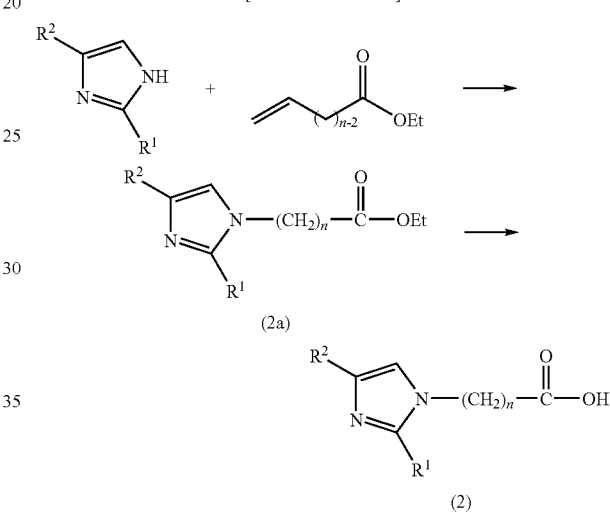

In the above Reaction Scheme 2, $R^1$, $R^2$ and n are the same as defined above.

According to the Reaction Scheme 2, Hetero-Michael addition reaction is performed between imidazole and ethyl alkenoate in the presence of $KF/Al_2O_3$ catalyst to obtain ethoxycarbonylalkylimidazole represented by the formula 2a in high yield. The Hetero-Michael addition reaction used in the present invention is a modified one of the method disclosed by Lei. Yang, Chun-Gu Xia et al. in *Tetrahedron Letters* 2005, 46, 3279-3283. Then, ethoxycarbonylalkylimidazole represented by the formula 2a is hydrolyzed to obtain imidazolylalkylcarboxylic acid represented by the formula 2.

Another reactant used in the present invention, the piperazine derivative represented by the formula 3, where Y is piperazinylalkylamine, was manufactured by a method shown in the Reaction Scheme 3 below.

[Reaction Scheme 3]

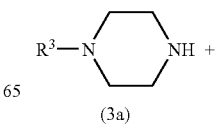

(3a)

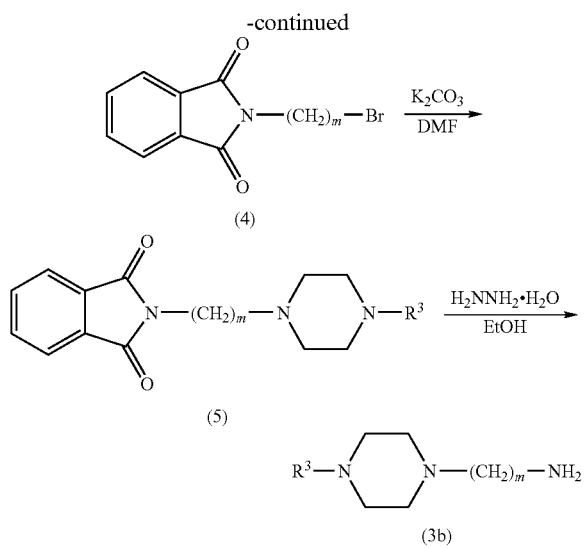

In the above Reaction Scheme 3, $R^3$, and m are the same as defined above.

According to the Reaction Scheme 3, a piperazine compound represented by the formula 3a with a substituent $R^3$, is reacted with bromoalkyl phthalimide represented by the formula 4 in a basic condition to obtain piperazinylalkylphthalimide represented by the formula 5. Then, the piperazinylalkylphthalimide represented by the formula 5 is reacted with hydrazine hydrate to obtain piperazine derivatives represented by the formula 3b.

The method used above is called Gabriel synthesis, a conventional method of amine synthesis (Gibson, M. S.; Bradshaw, R. W. *Angew. Chem. Int. Ed. Engl.* 1968, 7, 919).

The pharmaceutically acceptable salts of the imidazolylalkylcarbonyl derivatives represented by the formula 1 can be easily manufactured by using a conventional method disclosed in publications, and they can be also separated with high purity without further purification.

The method of manufacturing the pharmaceutically acceptable salts of the compounds represented by the above formula 1 is explained below with reference to a method of manufacturing hydrochloric acid salt. That is, an imidazolylalkylcarbonyl derivative represented by the formula 1 is dissolved in methylene chloride, and then added with about 1-10 eq. of hydrogen chloride solution to produce HCl salt, the target compound, in the form of a solid. The solvents to be used in manufacturing a hydrogen chloride solution are chloroform, methylene chloride, diethyl ether, methanol, ethyl acetate or a mixture thereof, preferably diethyl ether. The product obtained in the form of a solid can be separated by centrifugation or a solvent removing apparatus using cotton. After washing the solid with 1-2 mL of diethylether two or three times and drying, a high purity HCl salt can be obtained in the form of a solid.

The imidazolylalkylcarbonyl derivatives represented by the formula 1 or their pharmaceutically acceptable salts according to the present invention are effective as T-type calcium channel antagonist, and thus the present invention relates to a pharmaceutical composition comprising a novel compound represented by the formula 1 as an active ingredient.

Further, the pharmaceutical composition comprising imidazolylalkylcarbonyl derivatives represented by the formula 1 or their pharmaceutically acceptable salts as active ingredient according to the present invention is useful for the treatment and prevention of diseases due to their antagonistic activity against T-type calcium channel. Examples of the diseases due to T-type calcium channel antagonism are diabetes; cerebral diseases such as epilepsy, Parkinson's disease, and dementia; cardiac diseases such as hypertension, cardiac arrhythmia, angina pectoris, myocardial infarction, and congestive heart failure; pain-related diseases such as neuropathic pain, chronic and acute pains.

The pharmaceutical composition of the present invention comprising the compound represented by the formula 1 can be prepared in the form of tablets, capsules, troches, liquids, suspensions, etc., for oral or parenteral administration by adding a carrier, a reinforcing agent, and an excipient, etc.

The dosage of the compound represented by the formula 1 can vary depending on the age, body weight, sex, route of administration, health conditions, and severity of disease of a patient. In general, the dosage is 0.01-400 mg/day per an adult with 70 kg of body weight, may be administered from once to a few times a day at equal intervals according to a decision of a physician or a pharmacist.

The present invention is explained further in detail with reference to the method of manufacturing compounds and the efficacies of the products produced thereof based on the Examples and Experimental Examples. However, they should not be construed as limiting the scope of the present invention.

Further, the representing examples of synthesizing imidazolylalkylcarboxylic acid represented by the formula 2 and piperazine derivatives represented by the formula 3 are explained in the Preparation Examples below.

EXAMPLE

Preparation Example 1

Synthesis of Imidazolylalkylcarboxylic Acid (Formula 2)

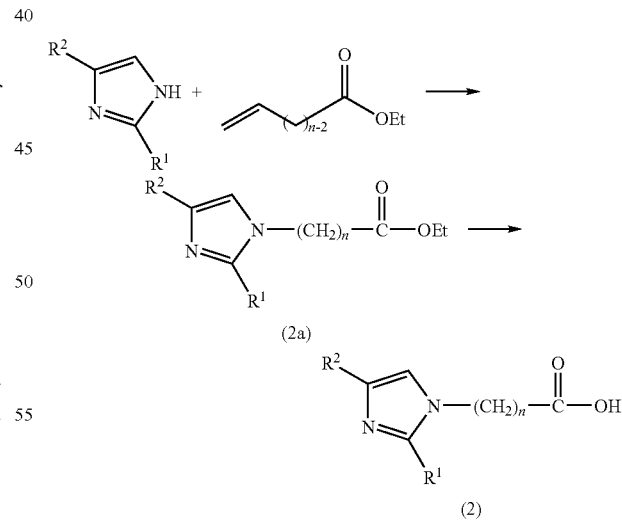

Preparation Example 1-1

3-(4-phenylimidazol-1-yl)propionic acid ethyl ester

4-Phenylimidazole (1.884 g, 13 mmol) and KF/Al$_2$O$_3$ (0.113 g, 10 mol %) were dissolved in 30 mL of CH$_3$CN, added with ethyl acrylate (1.301 g, 13 mmol) and stirred at room temperature. Initiation and termination of the reaction were confirmed by TLC (hexane:EtOAc=1:1). Upon completion of the reaction, $KF/Al_2O_3$ was filtrated under reduced pressure, water was added to the reaction mixture, and the aqueous phase was extracted with methylene chloride. The organic layer was dried with $MgSO_4$, filtrated and then concentrated under reduced pressure to obtain the target compound.

Yield 99.9%

$^1$H NMR (300 MHz, $CDCl_3$) δ 7.75 (d, J=7.07 Hz, 2H), 7.57 (s, 1H), 7.35 (t, J=5.14 Hz, 2H), 7.20 (m, 2H), 4.24 (t, J=6.50 Hz, 2H), 4.11 (q, J=2.45 Hz, 2H), 2.77 (t, J=9.38 Hz, 2H), 1.24 (t, J=12.80 Hz, 3H)

Preparation Example 1-2

3-(2-phenylimidazol-1-yl)propionic acid ethyl ester

Yield 99.9%

$^1$H NMR (300 MHz, $CDCl_3$) δ 7.48-7.51 (m, 2H), 7.32-7.37 (m, 3H), 4.24 (t, J=7.00 Hz, 2H), 4.01 (q, J=7.14 Hz, 2H), 2.61 (t, J=6.98 Hz, 2H), 1.16 (t, J=7.14 Hz, 3H)

Preparation Example 1-3

3-(4-methylimidazol-1-yl)propionic acid ethyl ester

Yield 99.9%

$^1$H NMR (300 MHz, $CDCl_3$) δ 7.21-7.28 (m, 1H), 6.48-6.58 (m, 1H), 3.94-4.04 (m, 4H), 2.54-2.59 (m, 2H), 2.04 (d, J=5.04 Hz, 3H), 1.08 (t, J=7.14 Hz, 3H)

Preparation Example 1-4

3-(2-methylimidazol-1-yl)propionic acid ethyl ester

Yield 99.9%

$^1$H NMR (300 MHz, $CDCl_3$) δ 6.55 (s, 2H), 3.78-3.87 (m, 4H), 2.42 (t, J=6.77 Hz, 2H), 2.08 (s, 3H), 0.92 (t, J=7.13 Hz, 3H)

Preparation Example 1-5

3-(4-phenylimidazol-1-yl)propionic acid 3-(4-phenylimidazol-1-yl)propionic acid ethyl ester (2.442 g, 10 mmol) was dissolved in 50 mL of ethanol, added with 0.5N-NaOH (20 mL) and then stirred at room temperature. Initiation and termination of the reaction was confirmed with TLC (EtOAc). Upon completion of the reaction, ethanol was removed by distillation under reduced pressure to obtain the target compound.

Yield 99.8%

$^1$H NMR (300 MHz, $CDCl_3$) δ 7.71 (m, 5H), 7.52 (s, 1H), 7.33 (t, J=13.65 Hz, 2H), 7.20 (t, J=13.35 Hz, 1H), 4.29 (t, J=6.76 Hz, 2H), 2.66 (t, J=6.76 Hz, 2H)

Preparation Example 2

Synthesis of Piperazinylalkylamine Derivatives (Formula 3b)

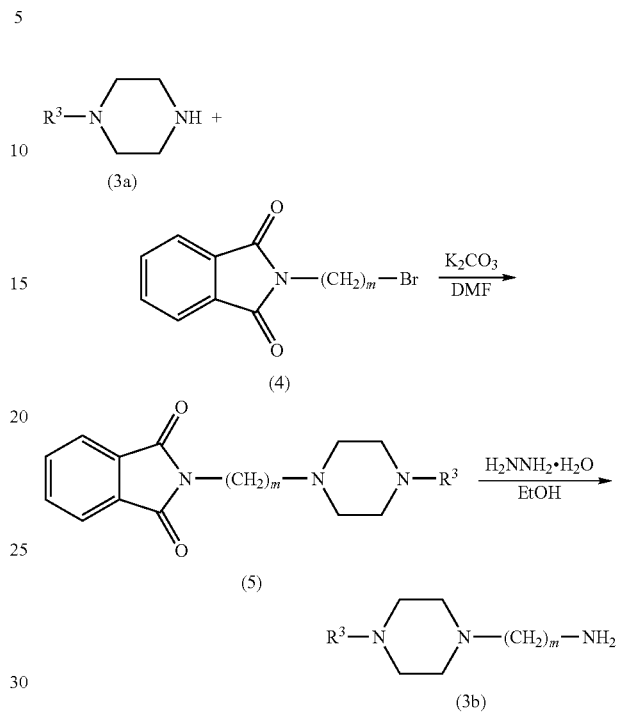

Piperazine derivatives 3a (10.00 mmol) and finely ground $K_2CO_3$ (30 mmol) were added into 50 mL of DMF and stirred at 80° C. Thirty minutes later, the reaction mixture was dropwisely added with N-bromoalkylphthalimide 4 (12 mmol) dissolved in 20 mL of DMF, and then stirred at 80° C. for 6 hours.

The initiation and termination of the reaction were confirmed with TLC (hexane:ethylacetate=3:1, v/v). Upon completion of the reaction, the reaction mixture was added with water, and then extracted with methylene chloride. The organic layer was dried with $MgSO_4$, filtrated and then concentrated under reduced pressure. The concentrate was purified by column chromatography (hexane:ethylacetate:methylene chloride=3:1:1, v/v/v) to obtain piperazinylalkylphthalimide 5.

The above obtained piperazinylalkylphthalimide (15.71 mmol) was added into 50 mL of ethanol and stirred with heating. When the reaction temperature reached 60° C., the reaction mixture was dropwisely added with hydrazine monohydrate (0.84 mL, 17.82 mmol), and stirred at 60° C. for 4 hours. The initiation and termination of the reaction were confirmed with TLC (methylene chloride:methanol=10:1, v/v). Upon completion of the reaction, the hot reaction mixture was filtered quickly under reduced pressure. The filtrate was distilled under reduced pressure, and the resulting solid was dissolved in water, and then washed with methylene chloride. The organic layer was dried with anhydrous magnesium sulfate, concentrated under reduced pressure to yield the piperazinylalkylamine derivative 3b.

Preparation Example 2-1

N-[2-(4-benzylpiperazin-1-yl)ethyl]phthalimide

Target compound was prepared according to the method same as in the Preparation Example 2 by using 4-benzylpiperazine as a piperazine derivative.

Yield 39%

¹H NMR (300 MHz, CDCl₃) δ 7.83-7.87 (m, 2H), 7.71-7.75 (m, 2H), 7.28-7.33 (m, 5H), 3.96 (t, J=6.71 Hz, 2H), 3.50 (m, 2H), 2.67 (m, 10H)

Preparation Example 2-2

N-{2-[4-(3-chlorobenzyl)piperazin-1-yl]ethyl}phthalimide

Target compound was prepared according to the method same as in the Preparation Example 2 by using 3-chlorobenzylpiperazine as a piperazine derivative.

Yield 62%

¹H NMR (300 MHz, CDCl₃) δ 7.74-7.79 (m, 2H), 7.63-7.67 (m, 2H), 7.13-7.27 (s, 4H), 3.89 (t, J=6.47 Hz, 2H), 3.53 (br, 2H), 2.59-2.63 (m, 8H)

Preparation Example 2-3

N-{2-[4-(3,4-dichlorobenzyl)piperazin-1-yl]ethyl}phthalimide

Target compound was prepared according to the method same as in the Preparation Example 2 by using 3,4-dichlorobenzylpiperazine as a piperazine derivative.

Yield 81%

¹H NMR (300 MHz, CDCl₃) δ 7.78-7.87 (m, 2H), 7.72-7.76 (m, 2H), 7.39 (m, 3H), 3.84 (t, J=6.65 Hz, 2H), 3.52 (br, 2H), 2.38-2.70 (m, 10H)

Preparation Example 24

N-{2-[4-(4-fluorobenzyl)piperazin-1-yl]ethyl}phthalimide

Target compound was prepared according to the method same as in the Preparation Example 2 by using 4-fluorobenzylpiperazine as a piperazine derivative.

Yield 59%

¹H NMR (300 MHz, CDCl₃) δ 7.82-7.85 (m, 2H), 7.67-7.74 (m, 2H), 7.22-7.27 (m, 2H), 6.94-7.00 (m, 2H), 3.89 (t, 2H), 3.42 (s, 2H), 2.63 (t, 2H), 2.39 (br, 4H), 2.04 (br, 4H)

Preparation Example 2-5

2-(4-benzylpiperazin-1-yl)ethylamine

Target compound was prepared according to the method same as in the Preparation Example 2 by using N-[2-(4-benzylpiperazin-1-yl)ethyl]phthalimide as a piperazinylalkylphthalimide derivative.

Yield 68%

¹H NMR (300 MHz, CDCl₃) δ 7.16-1.24 (m, 5H), 3.42 (m, 4H), 2.33 (m, 10H), 2.10 (s, 2H), 2.05 (s, 2H)

Preparation Example 2-6

2-[4-(3-chlorobenzyl)piperazin-1-yl]ethylamine

Target compound was prepared according to the method same as in the Preparation Example 2 by using N-{2-[4-(3-chlorobenzyl)piperazin-1-yl]ethyl}phthalimide as a piperazinylalkylphthalimide derivative.

Yield 63%

¹H NMR (300 MHz, CDCl₃) δ 7.33 (s, 1H), 7.18-7.23 (m, 3H), 3.49 (m, 2H), 2.79 (t, 2H), 2.43 (m, 10H), 1.55 (br, 2H)

Preparation Example 2-7

2-[4-(3,4-dichlorobenzyl)piperazin-1-yl]ethylamine

Target compound was prepared according to the method same as in the Preparation Example 2 by using N-{2-[4-(3,4-dichlorobenzyl)piperazin-1-yl]ethyl}phthalimide as a piperazinylalkylphthalimide derivative.

Yield 67%

¹H NMR (300 MHz, CDCl₃) δ 7.35-7.43 (m, 2H), 7.13-7.14 (d, 1H), 3.44 (s, 2H), 2.78 (t, J=6.258 Hz, 2H), 2.42 (m, 10H), 1.58 (s, 2H)

Preparation Example 2-8

2-[4-(4-fluorobenzylpiperazine)-1-yl]ethylamine

Target compound was prepared according to the method same as in the Preparation Example 2, by using N-{2-[4-(4-fluorobenzyl)piperazin-1-yl]ethyl}phthalimide as a piperazinylalkylphthalimide derivative.

Yield 36%

¹H NMR (300 MHz, CDCl₃) δ 7.25-7.29 (m, 2H), 6.96-7.03 (m, 2H), 3.46 (s, 2H), 2.78 (t, 2H), 2.39-2.42 (10H), 1.25 (s, 2H)

EXAMPLES

Synthesis of Imidazolylalkylcarbonyl Derivatives

Representative Example

Synthesis of 1-N-(4-substituted-piperazin-1-yl)carbonylalkylimidazole derivatives

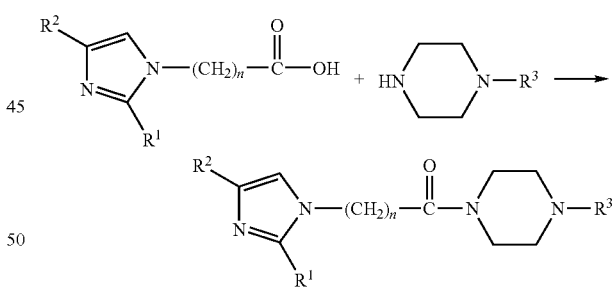

An imidazolylalkanoic acid (formula 2, 0.11 mmol) and 1-hydroxybenzotriazole (HOBt, 0.0149 g, 0.11 mmol) were added into a reaction container under a nitrogen atmosphere. A piperazine derivative (formula 3, 0.1 mmol) in 8 mL of purified CH₂Cl₂ was dropwisely added at 0° C. and stirred at room temperature for 3 hours. The initiation and termination of the reaction were confirmed with TLC (CH₂Cl₂:MeOH=20:1). Upon completion of the reaction, the reaction mixture was added with water and the aqueous layer was extracted with methylene chloride. The organic layer was dried with MgSO₄, filtered and then concentrated under reduced pressure. The resulting concentrate was purified by column chromatography (CH₂Cl₂:MeOH=20:1) to yield the target compound of the formula 1.

Example 1

Synthesis of 1-N-(4-diphenylmethylpiperazin-1-yl)carbonylethyl-4-phenylimidazole [Compound No. 1]

Yield 52.75%
$^1$H NMR (300 MHz, CDCl$_3$) δ 7.95 (s, 1H), 7.80 (d, J=7.43 Hz, 1H), 4.41 (t, J=6.07 Hz, 2H), 4.14 (s, 1H), 3.65 (s, 2H), 3.41 (s, 2H), 2.80 (t, J=6.06 Hz, 2H), 2.37 (s, 2H), 2.28 (s, 2H)

Example 2

Synthesis of 1-N-(4-benzylpiperazin-1-yl)carbonyl-ethyl-4-phenylimidazole [Compound No. 2]

Yield 77.30%
$^1$H NMR (300 MHz, CDCl$_3$) δ 7.65 (d, J=7.49 Hz, 2H), 7.55 (s, 1H), 7.30 (m, 10H), 4.32 (t, J=6.47 Hz, 2H), 3.62 (t, J=4.84 Hz, 2H), 3.43 (s, 2H), 3.33 (t, J=4.92 Hz, 2H), 2.73 (t, J=6.47 Hz, 2H), 2.38 (t, J=5.05 Hz, 2H), 2.28 (t, J=5.01 Hz, 2H)

Example 3

Synthesis of 1-N-[4-(2,3-dimethylphenyl)piperazin-1-yl]carbonylethyl-4-phenylimidazole [Compound No. 3]

Yield 63.70%
$^1$H NMR (300 MHz, CDCl$_3$) δ 7.79 (d, J=8.44 Hz, 2H), 7.59 (s, 1H), 7.38 (t, J=7.39 Hz, 2H), 7.29 (m, 2H), 7.03 (t, J=7.72 Hz, 1H), 6.95 (d, J=7.33 Hz, 1H), 6.78 (d, J=7.86 Hz, 1H), 4.38 (t, J=6.47 Hz, 2H), 3.78 (s, 2H), 3.51 (s, 2H), 2.81 (m, 6H), 2.25 (d, J=14.63 Hz, 6H)

Example 4

Synthesis of 1-N-[4-(2,4-dimethylphenyl)piperazin-1-yl]carbonylethyl-4-phenylimidazole [Compound No. 4]

Yield 66.0%
$^1$H NMR (300 MHz, CDCl$_3$) δ 7.78 (d, J=8.33 Hz, 2H), 7.59 (s, 1H), 7.35 (t, J=7.65 Hz, 2H), 7.25 (m, 2H), 6.99 (s, 1H), 6.92 (d, J=8.02 Hz, 1H), 6.77 (d, J=8.04 Hz, 1H), 4.35 (t, J=6.44 Hz, 2H), 3.74 (s, 2H), 3.46 (s, 2H), 2.75 (m, 6H), 2.25 (s, 6H)

Example 5

Synthesis of 1-N-[4-(4-chlorobenzyl)piperazin-1-yl]carbonylethyl-4-phenylimidazole [Compound No. 5]

Yield 67.5%
$^1$H NMR (300 MHz, CDCl$_3$) δ 7.79 (d, J=7.12 Hz, 2H), 7.53 (s, 1H), 7.39 (t, J=5.59 Hz, 2H), 7.19 (m, 6H), 4.32 (t, J=6.25 Hz, 2H), 3.61 (s, 2H), 3.32 (s, 2H), 2.71 (t, J=6.28 Hz, 2H), 2.30 (s, 2H), 2.18 (s, 2H)

Example 6

Synthesis of 1-N-[4-(4-chlorophenyl) (phenyl)methylpiperazin-1-yl]carbonylethyl-4-phenylimidazole [Compound No. 6]

Yield 51.9%
$^1$H NMR (300 MHz, CDCl$_3$) δ 7.79 (d, J=8.48 Hz, 2H), 7.54 (s, 1H), 7.39 (t, J=7.33 Hz, 2H), 7.20 (m, 1H), 4.34 (t, J=6.32 Hz, 2H), 4.06 (s, 1H), 3.61 (t, J=4.83 Hz, 2H), 3.33 (t, J=4.88 Hz, 2H), 2.72 (t, J=6.33 Hz, 2H), 2.31 (t, J=5.06 Hz, 2H), 2.19 (t, J=4.99 Hz, 2H)

Example 7

Synthesis of 1-N-[4-(4-fluorobenzyl)piperazin-1-yl]carbonylethyl-4-phenylimidazole [Compound No. 7]

Yield 50.20%
$^1$H NMR (300 MHz, CDCl$_3$) δ 7.77 (d, J=7.37 Hz, 2H), 7.57 (s, 1H), 7.38 (t, J=7.50 Hz, 2H), 7.23 (m, 4H), 6.99 (t, J=8.59 Hz, 2H), 4.37 (t, J=6.45 Hz, 2H), 3.63 (t, J=4.78 Hz, 2H), 3.37 (m, 4H), 2.78 (t, J=6.43 Hz, 2H), 2.43 (t, J=7.56 Hz, 2H), 2.36 (t, J=5.08 Hz, 2H)

Example 8

Synthesis of 1-N-[4-(3,4-dichlorobenzyl)piperazin-1-yl]carbonylethyl-4-phenylimidazole [Compound No. 8]

Yield 67.37%
$^1$H NMR (300 MHz, CDCl$_3$) δ 7.82 (d, J=1.31 Hz, 2H), 7.56 (s, 1H), 7.36 (m, 4H), 7.26 (m, 2H), 7.09 (d, J=1.85 Hz, 1H), 4.35 (t, J=6.41 Hz, 2H), 3.63 (t, J=4.87 Hz, 2H), 3.35 (s, 4H), 2.76 (t, J=6.40 Hz, 2H), 2.36 (t, J=5.10 Hz, 2H), 2.25 (t, J=5.02 Hz, 2H)

Example 9

Synthesis of 1-N-(4-ethylpiperazin-1-yl)carbonyl-ethyl-4-phenylimidazole [Compound No. 9]

Yield 63.62%
$^1$H NMR (300 MHz, CDCl$_3$) δ 7.76 (d, J=8.46 Hz, 2H), 7.56 (s, 1H), 7.36 (t, J=7.40 Hz, 2H), 7.24 (m, 2H), 4.35 (t, J=6.54 Hz, 2H), 3.64 (t, J=5.00 Hz, 2H), 3.38 (t, J=4.97 Hz, 2H), 2.77 (t, J=6.53 Hz, 2H), 2.38 (m, 6H), 1.05 (t, J=7.17 Hz, 3H)

Example 10

Synthesis of 1-N-(4-methylpiperazin-1-yl)carbonyl-ethyl-4-phenylimidazole [Compound No. 10]

Yield 45.14%
$^1$H NMR (300 MHz, CDCl$_3$) δ 7.75 (d, J=7.40 Hz, 2H), 7.55 (s, 1H), 7.33 (t, J=7.75 Hz, 2H), 7.22 (m, 2H), 4.34 (t, J=6.53 Hz, 2H), 3.63 (t, J=4.87 Hz, 2H), 3.37 (t, J=4.91 Hz, 2H), 2.76 (t, J=6.52 Hz, 2H), 2.30 (m, 7H)

Example 11

Synthesis of 1-N-[4-(2-hydroxyethyl)piperazin-1-yl]carbonylethyl-4-phenylimidazole [Compound No. 11]

Yield 48.40%
$^1$H NMR (300 MHz, CDCl$_3$) δ 7.75 (d, J=7.65 Hz, 2H), 7.57 (s, 1H), 7.37 (t, J=7.44 Hz, 2H), 7.23 (m, 2H), 4.37 (t, J=6.45 Hz, 2H), 3.62 (m, 4H), 3.39 (t, J=4.87 Hz, 2H), 2.78 (t, J=6.45 Hz, 2H), 2.46 (m, 7H)

Example 12

Synthesis of 1-N-(4-benzylpiperazin-1-yl)carbonyl-ethyl-2-phenylimidazole [Compound No. 12]

Yield 65.00%
$^1$H NMR (300 MHz, CDCl$_3$) δ 7.57 (d, J=7.65 Hz, 2H), 7.42 (m, 3H), 7.30 (m, 5H), 7.11 (s, 1H), 7.06 (s, 1H), 4.40 (t, J=7.16 Hz, 2H), 3.59 (t, J=4.94 Hz, 2H), 3.49 (s, 2H), 3.25 (t, J=4.94 Hz, 2H), 2.63 (t, J=7.20 Hz, 2H), 2.38 (t, J=5.14 Hz, 2H), 2.30 (t, J=5.08 Hz, 2H)

Example 13

Synthesis of 1-N-(4-diphenylmethylpiperazin-1-yl)carbonylethyl-2-phenylimidazole [Compound No. 13]

Yield 59.91%
$^1$H NMR (300 MHz, CDCl$_3$) δ 7.56 (d, J=1.40 Hz, 2H), 7.42 (m, 7H), 7.29 (m, 4H), 7.23 (m, 2H), 7.13 (s, 1H), 7.06 (s, 1H), 4.41 (t, J=7.15 Hz, 2H), 4.22 (s, 1H), 3.59 (t, J=4.96 Hz, 2H), 3.26 (t, J=4.96 Hz, 2H), 2.62 (t, J=7.19 Hz, 2H), 2.35 (t, J=5.15 Hz, 2H), 2.27 (t, J=5.07 Hz, 2H)

Example 14

Synthesis of 1-N-[4-(2-fluorophenyl)piperazin-1-yl]carbonylethyl-2-phenylimidazole [Compound No. 14]

Yield 87.00%
$^1$H NMR (300 MHz, CDCl$_3$) δ 7.59 (m, 2H), 7.42 (m, 2H), 7.08 (m, 4H), 7.05 (m, 1H), 6.88 (m, 1H), 4.34 (t, J=7.11 Hz, 2H), 3.74 (t, J=4.89 Hz, 2H), 3.41 (t, J=4.80 Hz, 2H), 2.99 (t, J=5.95 Hz, 2H), 2.92 (t, J=5.10 Hz, 2H), 2.68 (t, J=7.14 Hz, 2H)

Example 15

Synthesis of 1-N-[4-(2,3-dimethylphenyl)piperazin-1-yl]carbonylethyl-2-phenylimidazole [Compound No. 15]

Yield 57.59%
$^1$H NMR (300 MHz, CDCl$_3$) δ 7.62 (d, J=7.87 Hz, 2H), 7.48 (m, 3H), 7.11 (m, 3H), 6.95 (d, J=7.34 Hz, 1H), 4.46 (t, J=7.13 Hz, 2H), 3.42 (br, 2H), 2.76 (m, 6H), 2.28 (s, 3H), 2.22 (s, 3H)

Example 16

Synthesis of 1-N-[4-(2,4-dimethylphenyl)piperazin-1-yl]carbonylethyl-2-phenylimidazole [Compound No. 16]

Yield 38.03%
$^1$H NMR (300 MHz, CDCl$_3$) δ 7.61 (m, 2H), 7.44 (m, 3H), 7.14 (s, 1H), 7.10 (s, 1H), 6.97 (m, 2H), 6.85 (d, J=8.00 Hz, 1H), 4.46 (t, J=7.16 Hz, 2H), 3.73 (t, J=4.62 Hz, 2H), 3.40 (t, J=4.80 Hz, 2H), 2.80 (t, J=5.04 Hz, 2H), 2.75 (m, 4H), 2.28 (s, 6H)

Example 17

Synthesis of 1-N-[4-(4-chlorobenzyl)piperazin-1-yl]carbonylethyl-2-phenylimidazole [Compound No. 17]

Yield 66.50%
$^1$H NMR (300 MHz, CDCl$_3$) δ 7.55 (m, 2H), 7.41 (m, 3H), 7.26 (m, 4H), 7.09 (s, 1H), 7.05 (s, 1H), 4.39 (t, J=7.11 Hz, 2H), 3.56 (t, J=4.89 Hz, 2H), 3.43 (s, 2H), 3.24 (t, J=4.92 Hz, 2H), 2.63 (t, J=7.17 Hz, 2H), 2.35 (t, J=5.13 Hz, 2H), 2.27 (t, J=5.07 Hz, 2H)

Example 18

Synthesis of 1-N-[4-(3,4-dichlorobenzyl)piperazin-1-yl]carbonylethyl-2-phenylimidazole [Compound No. 18]

Yield 66.89%
$^1$H NMR (300 MHz, CDCl$_3$) δ 7.56 (d, J=7.74 Hz, 2H), 7.40 (m, 5H), 7.10 (s, 2H), 7.04 (s, 1H), 4.40 (t, J=7.08 Hz, 2H), 3.57 (t, J=4.86 Hz, 2H), 3.38 (s, 2H), 3.24 (t, J=4.89 Hz, 2H), 2.62 (t, J=7.14 Hz, 2H), 2.34 (t, J=5.13 Hz, 2H), 2.27 (t, J=5.04 Hz, 2H)

Example 19

Synthesis of 1-N-[4-(4-chlorophenyl) (phenyl)methylpiperazin-1-yl]carbonylethyl-2-phenylimidazole [Compound No. 19]

Yield 67.32%
$^1$H NMR (300 MHz, CDCl$_3$) δ 7.56 (d, J=1.47 Hz, 2H), 7.42 (m, 2H), 7.31 (m, 9H), 7.12 (s, 1H), 7.05 (s, 1H), 4.41 (t, J=7.11 Hz, 2H), 4.20 (s, 1H), 3.57 (t, J=4.58 Hz, 2H), 3.26 (t, J=4.93 Hz, 2H), 2.62 (t, J=7.15 Hz, 2H), 2.33 (t, J=5.04 Hz, 2H), 2.25 (t, J=5.15 Hz, 2H)

Example 20

Synthesis of 1-N-[4-(2-fluorophenyl)piperazin-1-yl]carbonylethyl-4-phenylimidazole No. 20]

Yield 42.75%
$^1$H NMR (300 MHz, CDCl$_3$) δ 7.76 (d, J=8.45 Hz, 2H), 7.57 (s, 1H), 7.36 (t, J=7.32 Hz, 2H), 7.00-7.03 (m, 3H), 6.82-6.99 (m, 1H), 4.36 (t, J=6.45 Hz, 2H), 3.78 (t, J=4.92 Hz, 2H), 3.51 (t, J=4.86 Hz, 2H), 3.00 (t, J=5.14 Hz, 2H), 2.94 (t, J=5.09 Hz, 2H), 2.80 (t, J=6.44 Hz, 2H)

Example 21

Synthesis of 1-N-[4-(4-fluorobenzyl)piperazin-1-yl]carbonylethyl-2-phenylimidazole [Compound No. 21]

Yield 69.49%
$^1$H NMR (300 MHz, CDCl$_3$) δ 7.56 (d, J=7.68 Hz, 2H), 7.41 (m, 3H), 7.23 (m, 2H), 7.09 (s, 1H), 7.05 (s, 1H), 7.00 (t, J=8.67 Hz, 2H), 4.39 (t, J=7.11 Hz, 2H), 3.56 (t, J=4.92 Hz, 2H), 3.42 (s, 2H), 3.23 (t, J=4.92 Hz, 2H), 2.62 (t, J=7.14 Hz, 2H), 2.34 (t, J=5.10 Hz, 2H), 2.26 (t, J=5.07 Hz, 2H)

Example 22

Synthesis of 1-N-(4-methylpiperazin-1-yl)carbonylethyl-2-phenylimidazole [Compound No. 22]

Yield 59.05%
$^1$H NMR (300 MHz, CDCl$_3$) δ 7.56 (d, J=6.27 Hz, 2H), 7.42 (m, 3H), 7.10 (s, 1H), 7.05 (s, 1H), 4.40 (t, J=7.17 Hz, 2H), 3.58 (t, J=4.98 Hz, 2H), 3.26 (t, J=4.98 Hz, 2H), 2.63 (t, J=7.23 Hz, 2H), 2.32 (t, J=5.16 Hz, 2H), 2.26 (t, J=4.65 Hz, 5H)

Example 23

Synthesis of 1-N-(4-ethylpiperazin-1-yl)carbonylethyl-2-phenylimidazole [Compound No. 23]

Yield 56.53%
$^1$H NMR (300 MHz, CDCl$_3$) δ 7.56 (m, 2H), 7.41 (m, 3H), 7.07 (s, 1H), 7.03 (s, 1H), 4.37 (t, J=7.17 Hz, 2H), 3.56 (t, J=4.98 Hz, 2H), 3.24 (t, J=4.95 Hz, 2H), 2.61 (t, J=7.23 Hz, 2H), 2.37 (t, J=7.23 Hz, 2H), 2.33 (m, 4H), 2.26 (t, J=5.10 Hz, 2H), 1.03 (t, J=7.17 Hz, 3H)

Example 24

Synthesis of 1-N-[4-(2-hydroxyethyl)piperazin-1-yl]carbonylethyl-2-phenylimidazole [Compound No. 24]

Yield 81.00%
$^1$H NMR (300 MHz, CDCl$_3$) δ 7.58 (m, 2H), 7.44 (m, 3H), 7.07 (d, J=11.01 Hz, 2H), 4.40 (t, J=7.17 Hz, 2H), 3.60 (t, J=5.94 Hz, 4H), 3.26 (t, J=5.19 Hz, 2H), 2.63 (t, J=7.14 Hz, 2H), 2.51 (t, J=5.52 Hz, 2H), 2.42 (t, J=5.19 Hz, 2H), 2.36 (t, J=5.22 Hz, 4H)

Example 25

Synthesis of 1-N-[4-(3-chlorophenyl)piperazin-1-yl]carbonylethyl-4-phenylimidazole [Compound No. 25]

Yield 40.50%
$^1$H NMR (300 MHz, CDCl$_3$) δ 7.74 (d, J=7.37 Hz, 2H), 7.56 (s, 1H), 7.35 (t, J=7.40 Hz, 2H), 7.15-7.26 (m, 3H), 6.81-6.86 (m, 2H), 6.70 (d, J=7.20 Hz, 1H), 4.36 (t, J=6.45 Hz, 2H), 3.75 (t, J=4.93 Hz, 2H), 3.47 (t, J=4.83 Hz, 2H), 3.12 (t, J=5.24 Hz, 2H), 3.05 (t, J=5.18 Hz, 2H), 2.23 (t, J=6.12 Hz, 2H)

Example 26

Synthesis of 1-N-[4-(3-chlorophenyl)piperazin-1-yl]carbonylethyl-2-phenylimidazole [Compound No. 26]

Yield 18.57%
$^1$H NMR (300 MHz, CDCl$_3$) δ 7.48-7.50 (m, 4H), 7.00 (s, 2H), 6.60-6.69 (m, 4H), 4.01 (t, J=6.45 Hz, 2H), 3.43 (t, J=4.93 Hz, 4H), 3.35 (t, J=4.83 Hz, 4H), 2.23 (t, J=6.12 Hz, 2H)

Example 27

Synthesis of 1-N-[4-(4-methoxyphenyl)piperazin-1-yl]carbonylethyl-4-phenylimidazole [Compound No. 27]

Yield 63.19%
$^1$H NMR (300 MHz, CDCl$_3$) δ 7.77 (s, 1H), 7.72 (d, J=1.96 Hz, 2H), 7.38 (t, J=1.40 Hz, 2H), 7.29 (q, J=3.50 Hz, 2H), 6.83 (s, 4H), 4.38 (t, J=6.36 Hz, 2H), 3.73-3.76 (m, 5H), 3.50 (t, J=4.69 Hz, 2H), 2.98 (t, J=5.16 Hz, 2H), 2.93 (t, J=5.08 Hz, 2H), 2.83 (t, J=6.36 Hz, 2H)

Example 28

Synthesis of 1-N-[4-(4-methoxyphenyl)piperazin-1-yl]carbonylethyl-2-phenylimidazole [Compound No. 28]

Yield 90.52%
$^1$H NMR (300 MHz, CDCl$_3$) δ 7.71-7.74 (m, 2H), 7.49 (s, 2H), 7.38-7.41 (m, 2H), 6.83 (s, 4H), 4.40 (t, J=6.74 Hz, 2H), 3.76 (s, 3H), 3.70 (t, J=4.98 Hz, 2H), 3.45 (t, J=4.78 Hz, 2H), 2.97 (t, J=5.20 Hz, 2H), 2.92 (t, J=5.12 Hz, 2H), 2.79 (t, J=6.73 Hz, 2H)

Example 29

Synthesis of 1-N-(4-phenylpiperazin-1-yl)carbonylethyl-4-methylimidazole [Compound No. 29]

Yield 50.34%
$^1$H NMR (300 MHz, CDCl$_3$) δ 7.40-7.49 (m, 1H), 7.27 (t, J=6.66 Hz, 2H), 6.88-6.92 (m, 3H), 6.66-6.74 (m, 1H), 4.24 (q, J=6.90 Hz, 2H), 3.75 (t, J=4.95 Hz, 2H), 3.49 (q, J=5.52 Hz, 2H), 3.06-3.13 (m, 4H), 2.74 (q, J=6.72 Hz, 2H), 2.21 (s, 1H), 2.18 (s, 2H)

Example 30

Synthesis of 1-N-(4-diphenylmethylpiperazin-1-yl)carbonylethyl-4-methylimidazole M [Compound No. 30]

Yield 42.68%
$^1$H NMR (300 MHz, CDCl$_3$) δ 7.40 (d, J=1.05 Hz, 5H), 7.27 (t, J=7.06 Hz, 4H), 7.17 (d, J=8.65 Hz, 2H), 6.67-6.74 (m, 1H), 4.20 (q, J=7.05 Hz, 3H), 3.60 (t, J=4.67 Hz, 2H), 3.30 (q, J=4.61 Hz, 2H), 2.65 (q, J=6.22 Hz, 2H), 2.35 (t, J=4.70 Hz, 2H), 2.30 (d, J=3.96 Hz, 2H), 2.19 (d, J=4.23 Hz, 3H)

Example 31

Synthesis of 1-N-(4-benzylpiperazin-1-yl)carbonylethyl-4-methylimidazole [Compound No. 31]

Yield 63.46%
$^1$H NMR (300 MHz, CDCl$_3$) δ 7.38-7.45 (m, 1H), 7.22-7.33 (m, 5H), 6.69 (d, J=12.09 Hz, 1H), 4.20 (q, J=7.56 Hz, 2H), 3.60 (t, J=4.92 Hz, 2H), 3.48 (s, 2H), 3.31 (q, J=4.71 Hz, 2H), 2.67 (q, J=7.56 Hz, 2H), 2.39 (t, J=4.89 Hz, 2H), 2.32 (t, J=4.86 Hz, 2H), 2.19 (s, 3H)

Example 32

Synthesis of 1-N-[4-(2,3-dimethylphenyl)piperazin-1-yl]carbonylethyl-4-methylimidazole [Compound No. 32]

Yield 69.08%
$^1$H NMR (300 MHz, CDCl$_3$) δ 7.40-7.47 (m, 1H), 7.08 (t, J=7.68 Hz, 1H), 6.93 (d, J=7.39 Hz, 1H), 6.84 (d, J=7.93 Hz, 1H), 6.72 (m, 1H), 4.26 (q, J=7.07 Hz, 2H), 3.50 (br, 2H), 2.73-2.91 (m, 6H), 2.21-2.27 (m, 11H)

Example 33

Synthesis of 1-N-(4-benzylpiperazin-1-yl)carbonylethyl-2-methylimidazole [Compound No. 33]

Yield 59.82%
$^1$H NMR (300 MHz, CDCl$_3$) δ 7.22-7.32 (m, 5H), 6.85 (s, 1H), 6.82 (s, 1H), 4.17 (t, J=6.99 Hz, 2H), 3.58 (t, J=4.89 Hz, 2H), 3.47 (s, 2H), 3.30 (t, J=4.92 Hz, 2H), 2.65 (t, J=6.96 Hz, 2H), 2.35-2.39 (m, 5H), 2.31 (t, J=5.04 Hz, 2H)

Example 34

Synthesis of 1-N-(4-phenylpiperazin-1-yl)carbonylethyl-2-methylimidazole [Compound No. 34]

Yield 62.20%
$^1$H NMR (300 MHz, CDCl$_3$) δ 7.28-7.23 (m, 2H), 6.85-6.91 (m, 5H), 4.22 (t, J=6.99 Hz, 2H), 3.74 (t, J=5.07 Hz, 2H), 3.47 (t, J=4.92 Hz, 2H), 3.05-3.13 (m, 4H), 2.72 (t, J=6.96 Hz, 2H), 2.38 (d, J=4.38 Hz, 3H)

Example 35

Synthesis of 1-N-(4-diphenylmethylpiperazin-1-yl) carbonylethyl-2-methylimidazole [Compound No. 35]

Yield 62.50%
$^1$H NMR (300 MHz, CDCl$_3$) δ 7.38 (d, J=7.05 Hz, 4H), 7.25 (t, J=6.18 Hz, 4H), 7.16-7.19 (m, 2H), 6.86 (s, 1H), 4.13-4.20 (m, 3H), 3.58 (t, J=4.83 Hz, 2H), 3.28 (t, J=4.80 Hz, 2H), 2.62 (t, J=6.90 Hz, 2H), 2.31-2.37 (m, 5H), 2.27 (t, J=4.98 Hz, 2H)

Example 36

Synthesis of 1-N-[4-(2,3-dimethylphenyl)piperazin-1-yl]carbonylethyl-2-methylimidazole [Compound No. 36]

Yield 59.00%
$^1$H NMR (300 MHz, CDCl$_3$) δ 7.07 (t, J=7.69 Hz, 1H), 6.83-6.94 (m, 4H), 4.25 (t, J=6.99 Hz, 2H), 3.50 (br, 2H), 2.71-2.83 (m, 8H), 2.41 (s, 3H), 2.27 (s, 3H), 2.22 (s, 3H)

Example 37

Synthesis of 1-N-[4-(2,4-dimethylphenyl)piperazin-1-yl]carbonylethyl-2-methylimidazole [Compound No. 37]

Yield 50.22%
$^1$H NMR (300 MHz, CDCl$_3$) δ 6.97 (t, J=8.17 Hz, 2H), 6.87 (t, J=7.16 Hz, 3H), 4.24 (t, J=6.99 Hz, 2H), 3.74 (t, J=4.59 Hz, 2H), 3.47 (t, J=4.77 Hz, 2H), 2.72-2.83 (m, 6H), 2.40 (s, 3H), 2.26 (s, 6H)

Example 38

Synthesis of 1-N-[4-(2,4-dimethylphenyl)piperazin-1-yl]carbonylethyl-4-methylimidazole [Compound No. 38]

Yield 40.61%
$^1$H NMR (300 MHz, CDCl$_3$) δ 7.45 (m, 1H), 6.98 (t, J=7.02 Hz, 2H), 6.86 (d, J=8.00 Hz, 1H), 6.67-6.76 (m, 1H), 4.26 (q, J=6.99 Hz, 2H), 3.74 (t, J=4.58 Hz, 2H), 3.48 (q, J=5.03 Hz, 2H), 2.72-2.83 (m, 6H), 2.27 (s, 6H), 2.21 (d, J=6.93 Hz, 3H)

Example 39

Synthesis of 1-N-[4-(2-fluorophenyl)piperazin-1-yl]carbonylethyl-2-methylimidazole [Compound No. 39]

Yield 51.58%
$^1$H NMR (300 MHz, CDCl$_3$) δ 6.85-7.05 (m, 6H), 4.22 (t, J=6.96 Hz, 2H), 3.76 (t, J=5.01 Hz, 2H), 3.49 (t, J=4.92 Hz, 2H), 2.93-3.02 (m, 4H), 2.73 (t, J=6.87 Hz, 2H), 2.37 (s, 3H)

Example 40

Synthesis of 1-N-[4-(2-fluorophenyl)piperazin-1-yl]carbonylethyl-4-methylimidazole [Compound No. 40]

Yield 53.85%
$^1$H NMR (300 MHz, CDCl$_3$) δ 7.46-7.39 (m, 1H), 6.96-7.04 (m, 4H), 6.65-6.74 (m, 1H), 4.25 (t, J=6.75 Hz, 2H), 3.76 (t, J=5.01 Hz, 2H), 3.50 (q, J=4.86 Hz, 2H), 2.94-3.02 (m, 4H), 2.70-2.77 (m, 2H), 2.18 (d, J=8.64 Hz, 3H)

Example 41

Synthesis of 1-N-[4-(4-chlorobenzyl)piperazin-1-yl] carbonylethyl-2-methylimidazole [Compound No. 41]

Yield 55.14%
$^1$H NMR (300 MHz, CDCl$_3$) δ 7.19-7.27 (m, 4H), 6.85 (s, 1H), 6.82 (s, 1H), 4.18 (t, J=6.96 Hz, 2H), 3.58 (t, J=4.83 Hz, 2H), 3.42 (s, 2H), 3.29 (t, J=4.83 Hz, 2H), 2.66 (t, J=6.96 Hz, 2H), 2.39 (s, 5H), 2.28 (t, J=5.01 Hz, 2H)

Example 42

Synthesis of 1-N-[4-(4-chlorobenzyl)piperazin-1-yl] carbonylethyl-4-methylimidazole No. 42]

Yield 58.44%
$^1$H NMR (300 MHz, CDCl$_3$) δ 7.36-7.42 (m, 1H), 7.19-7.27 (m, 4H), 6.61-6.71 (m, 1H), 4.20 (t, J=6.75 Hz, 2H), 3.57 (t, J=4.86 Hz, 2H), 3.42 (s, 3H), 3.31 (t, J=5.58 Hz, 2H), 2.67 (t, J=6.75 Hz, 2H), 2.35 (t, J=4.98 Hz, 2H), 2.28 (t, J=4.89 Hz, 2H), 2.17 (s, 3H)

Example 43

Synthesis of 1-N-[4-(4-fluorobenzyl)piperazin-1-yl] carbonylethyl-2-methylimidazole [Compound No. 43]

Yield 55.41%
$^1$H NMR (300 MHz, CDCl$_3$) δ 7.20-7.24 (m, 2H), 6.95 (t, J=8.73 Hz, 2H), 6.84 (s, 1H), 4.17 (t, J=6.96 Hz, 2H), 3.56 (t, J=4.98 Hz, 2H), 3.41 (s, 1H), 3.29 (t, J=4.92 Hz, 2H), 2.65 (t, J=6.96 Hz, 2H), 2.32 (s, 5H), 2.28 (t, J=5.19 Hz, 2H)

Example 44

Synthesis of 1-N-[4-(4-fluorobenzyl)piperazin-1-yl] carbonylethyl-4-methylimidazole [Compound No. 44]

Yield 51.95%
$^1$H NMR (300 MHz, CDCl$_3$) δ 7.35-7.41 (m, 1H), 7.20-7.27 (m, 2H), 6.96 (t, J=8.58 Hz, 2H), 6.61-6.70 (m, 1H), 4.18 (q, J=7.32 Hz, 2H), 3.57 (t, J=5.04 Hz, 2H), 3.41 (s, 2H), 3.30 (q, J=4.65 Hz, 2H), 2.67 (t, J=6.57 Hz, 2H), 2.34 (t, J=5.07 Hz, 2H), 2.28 (t, J=4.92 Hz, 2H), 2.16 (s, 3H)

Example 45

Synthesis of 1-N-[4-(4-chlorophenyl) (phenyl)methylpiperazin-1-yl]carbonylethyl-4-methylimidazole [Compound No. 45]

Yield 61.49%
$^1$H NMR (300 MHz, CDCl$_3$) δ 7.19-7.43 (m, 10H), 6.62-6.73 (m, 1H), 4.19 (q, J=6.12 Hz, 2H), 3.59 (t, J=4.47 Hz, 2H), 3.30-3.34 (m, 2H), 2.66 (t, J=6.39 Hz, 2H), 2.32 (t, J=4.86 Hz, 2H), 2.27 (s, 2H), 2.18 (d, J=4.02 Hz, 3H)

Example 46

Synthesis of 1-N-[4-(4-chlorophenyl) (phenyl)methylpiperazin-1-yl]carbonylethyl-2-methylimidazole [Compound No. 46]

Yield 67.91%
$^1$H NMR (300 MHz, CDCl$_3$) δ 7.16-7.34 (m, 9H), 6.87 (s, 1H), 6.81 (s, 1H), 4.13-4.20 (m, 3H), 3.59 (t, J=4.83 Hz, 2H), 3.30 (t, J=4.86 Hz, 2H), 2.64 (t, J=6.90 Hz, 2H), 2.38 (s, 3H), 2.32 (t, J=5.04 Hz, 2H), 2.26 (t, J=4.98 Hz, 2H)

Example 47

Synthesis of 1-N-[4-(3,4-dichlorobenzyl)piperazin-1-yl]carbonylethyl-2-methylimidazole [Compound No. 47]

Yield 74.91%
$^1$H NMR (300 MHz, CDCl$_3$) δ 7.39-7.34 (m, 2H), 7.11 (d, J=6.33 Hz, 1H), 6.85 (s, 1H), 6.82 (s, 1H), 4.19 (t, J=6.96 Hz, 2H), 3.59 (t, J=4.83 Hz, 2H), 3.41 (s, 2H), 3.31 (t, J=4.83 Hz, 2H), 2.66 (t, J=6.93 Hz, 2H), 2.36 (s, 5H), 2.39 (t, J=5.01 Hz, 2H)

Example 48

Synthesis of 1-N-[4-(3,4-dichlorobenzyl)piperazin-1-yl]carbonylethyl-4-methylimidazole [Compound No. 48]

Yield 53.56%
$^1$H NMR (300 MHz, CDCl$_3$) δ 7.33-7.42 (m, 3H), 7.11 (d, J=6.27 Hz, 1H), 6.61-6.71 (m, 1H), 4.20 (t, J=6.72 Hz, 2H), 3.58 (t, J=5.01 Hz, 2H), 3.41 (s, 2H), 3.32 (t, J=5.85 Hz, 2H), 2.68 (t, J=6.57 Hz, 2H), 2.35 (t, J=5.10 Hz, 2H), 2.28 (t, J=5.10 Hz, 2H), 2.16 (s, 3H)

Example 49

Synthesis of 1-N-[4-(3-chlorophenyl)piperazin-1-yl]carbonylethyl-2-methylimidazole [Compound No. 49]

Yield 45.24%
$^1$H NMR (300 MHz, CDCl$_3$) δ 7.80 (d, J=8.16 Hz, 1H), 7.61 (d, J=8.10 Hz, 1H), 7.24-7.31 (m, 3H), 7.12-7.15 (m, 1H), 4.25 (t, J=6.45 Hz, 2H), 3.68 (t, J=5.76 Hz, 2H), 3.45 (t, J=4.02 Hz, 2H), 3.03-3.11 (m, 4H), 2.78 (t, J=6.42 Hz, 2H), 2.48 (s, 3H)

Example 50

Synthesis of 1-N-[4-(3-chlorophenyl)piperazin-1-yl]carbonylethyl-4-methylimidazole [Compound No. 50]

Yield 49.20%
$^1$H NMR (300 MHz, CDCl$_3$) δ 7.33-7.42 (m, 4H), 7.11 (d, J=6.27 Hz, 1H), 6.61-6.71 (m, 1H), 4.22-4.28 (m, 2H), 3.59-3.61 (m, 2H), 3.39-3.42 (m, 2H), 2.97-3.03 (m, 4H), 2.77-2.79 (m, 2H), 2.08-2.18 (m, 3H)

Example 51

Synthesis of 1-N-[4-(4-methoxyphenyl)piperazin-1-yl]carbonylethyl-2-methylimidazole [Compound No. 51]

Yield 39.57%
$^1$H NMR (300 MHz, CDCl$_3$) δ 7.57-7.76 (m, 2H), 7.19-7.29 (m, 3H), 7.07 (s, 1H), 6.96 (s, 1H), 4.24 (t, J=6.33 Hz, 2H), 3.72 (s, 3H), 3.66 (t, J=4.59 Hz, 2H), 3.45 (t, J=4.77 Hz, 2H), 2.88-2.95 (m, 4H), 2.79 (t, J=6.33 Hz, 2H), 2.50 (s, 3H)

Example 52

Synthesis of 1-N-[4-(4-methoxyphenyl)piperazin-1-yl]carbonylethyl-4-methylimidazole [Compound No. 52]

Yield 61.30%
$^1$H NMR (300 MHz, CDCl$_3$) δ 7.53-7.70 (m, 3H), 7.17-7.22 (m, 3H), 3.68 (s, 3H), 3.62 (br, 2H), 3.41 (br, 2H), 3.36 (br, 4H), 2.81-2.88 (m, 4H), 2.07-2.18 (m, 3H)

Example 53

Synthesis of 1-N-(4-phenylpiperazin-1-yl)carbonylethyl-4-phenylimidazole [Compound No. 53]

Yield 50.01%
$^1$H NMR (300 MHz, CDCl$_3$) δ 7.75-7.78 (m, 1H), 7.59 (s, 1H), 7.34-7.39 (m, 2H), 7.21-7.30 (m, 5H), 6.88-6.94 (m, 3H), 4.40 (t, J=6.55 Hz, 2H), 3.80 (t, J=5.07 Hz, 2H), 3.54 (t, J=4.99 Hz, 2H), 3.09-3.17 (m, 4H), 2.85 (t, J=6.50 Hz, 2H)

Example 54

Synthesis of 1-N-(4-phenylpiperazin-1-yl)carbonylethyl-2-phenylimidazole [Compound No. 54]

Yield 51.20%
$^1$H NMR (300 MHz, CDCl$_3$) δ 7.59-7.62 (m, 2H), 7.45-7.47 (m, 3H), 7.25-7.31 (m, 2H), 7.12 (s, 1H), 7.09 (s, 1H), 6.89-6.93 (m, 3H), 4.45 (t, J=7.23 Hz, 2H), 3.74 (t, J=4.95 Hz, 2H), 3.40-3.43 (m, 2H), 3.03-3.14 (m, 4H), 2.70 (t, J=7.23 Hz, 2H)

Representative Example

Synthesis of N-[m-(4-substituted-piperazin-1-yl)alkyl]carbamoylalkylimidazole derivatives

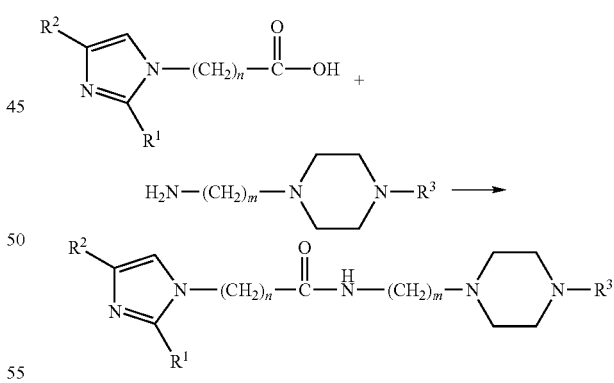

An imidazolylalkanoic acid (0.1 mmol), EDC (0.0211 g, 0.11 mmol), and HOBt (0.0149 g, 0.11 mmol) were added into a reaction container under a nitrogen atmosphere. A piperazinylalkylamine (0.1 mmol) in 8 mL of purified CH$_2$Cl$_2$ was dropwisely added at 0° C. and stirred at room temperature for 3 hours. The initiation and termination of the reaction were confirmed with TLC (CH$_2$Cl$_2$:MeOH=15:1). Upon completion of the reaction, the reaction mixture was added with water and the aqueous layer was extracted with methylene chloride. The organic layer was dried with MgSO$_4$, filtrated and then concentrated under reduced pressure. The resulting

Example 55

Synthesis of 1-N-[2-(4-diphenylmethylpiperazin-1-yl)ethyl]carbamoylethyl-4-phenylimidazole [Compound No. 55]

Yield 31.20%
$^1$H NMR (300 MHz, CDCl$_3$) δ 7.72 (s, 1H), 7.69 (s, 1H), 7.49 (s, 1H), 7.24 (m, 14H), 6.53 (br, 1H), 4.30 (t, J=6.18 Hz, 2H), 4.11 (s, 1H), 3.33 (q, J=11.00 Hz, 2H), 2.64 (t, J=6.31 Hz, 2H), 2.44 (m, 6H), 2.28 (br, 4H)

Example 56

Synthesis of 1-N-{2-[4-(2,3-dimethylphenyl) (phenyl)methylpiperazin-1-yl]ethyl}carbamoylethyl-4-phenylimidazole [Compound No. 56]

Yield 32.92%
$^1$H NMR (300 MHz, CDCl$_3$) δ 7.77 (d, J=1.26 Hz, 2H), 7.52 (s, 1H), 7.35 (t, J=7.34 Hz, 2H), 7.25 (m, 2H), 7.05 (t, J=Hz, 1H), 6.90 (d, J=7.35 Hz, 2H), 6.79 (d, J=7.91 Hz, 1H), 6.23 (br, 1H), 4.34 (t, J=6.07 Hz, 2H), 3.36 (q, J=5.43 Hz, 2H), 2.77 (t, J=4.31 Hz, 4H), 2.65 (t, J=6.24 Hz, 2H), 2.47 (m, 6H), 2.27 (s, 3H), 2.17 (s, 3H)

Example 57

Synthesis of 1-N-[2-[4-(3-chlorobenzyl)piperazin-1-yl]ethyl]carbamoylethyl-4-phenylimidazole [Compound No. 57]

Yield 46.76%
$^1$H NMR (300 MHz, CDCl$_3$) δ 7.74 (d, J=1.30 Hz, 2H), 7.47 (s, 1H), 7.34 (t, J=7.35 Hz, 2H), 7.27 (d, J=1.75 Hz, 1H), 7.21 (m, 4H), 7.13 (m, 1H), 6.33 (br, 1H), 4.29 (t, J=6.12 Hz, 2H), 3.36 (s, 1H), 3.28 (q, J=5.61 Hz, 2H), 2.60 (t, J=6.30 Hz, 2H), 2.41 (m, 10H)

Example 58

Synthesis of 1-N-[2-[4-(3,4-dichlorobenzyl)piperazin-1-yl]ethyl]carbamoylethyl-4-phenylimidazole [Compound No. 58]

Yield 55.03%
$^1$H NMR (300 MHz, CDCl$_3$) δ 7.71 (d, J=8.43 Hz, 2H), 7.45 (s, 1H), 7.30 (m, 4H), 7.20 (m, 2H), 7.06 (d, J=8.19 Hz, 1H), 6.37 (br, 1H), 4.28 (t, J=6.09 Hz, 2H), 3.31 (m, 4H), 2.59 (t, J=6.24 Hz, 2H), 2.39 (m, 10H)

Example 59

Synthesis of 1-N-[2-[4-(3,4-dichlorobenzyl)piperazin-1-yl]ethyl]carbamoylethyl-2-phenylimidazole [Compound No. 59]

Yield 53.00%
$^1$H NMR (300 MHz, CDCl$_3$) δ 7.58 (m, 2H), 7.42 (m, 5H), 7.15 (m, 1H), 7.05 (d, J=9.48 Hz, 2H), 6.17 (br, 1H), 4.37 (t, J=6.73 Hz, 2H), 3.44 (s, 2H), 3.28 (q, J=11.19 Hz, 2H), 2.49 (t, J=6.71 Hz, 2H), 2.40 (m, 10H)

Example 60

Synthesis of 1-N-[2-[4-(3-chlorobenzyl)piperazin-1-yl]ethyl]carbamoylethyl-2-phenylimidazole [Compound No. 60]

Yield 47.23%
$^1$H NMR (300 MHz, CDCl$_3$) δ 7.51 (m 2H), 7.39 (m, 3H), 7.29 (s, 1H), 7.20 (m, 3H), 7.00 (d, J=7.07 Hz, 2H), 6.56 (br, 1H), 4.30 (t, J=6.77 Hz, 2H), 3.37 (s, 2H), 3.24 (q, J=10.97 Hz, 2H), 2.39 (m, 12H)

Example 61

Synthesis of 1-N-[2-[4-(2,4-dimethylphenyl)piperazin-1-yl]ethyl]carbamoylethyl-4-phenylimidazole [Compound No. 61]

Yield 41.09%
$^1$H NMR (300 MHz, CDCl$_3$) δ 7.76 (d, J=7.13 Hz, 2H), 7.52 (s, 1H), 7.35 (t, J=7.35 Hz, 2H), 7.26 (m, 2H), 6.96 (t, J=6.34 Hz, 2H), 6.79 (d, J=7.99 Hz, 2H), 6.46 (br, 1H), 4.33 (t, J=6.18 Hz, 2H), 3.36 (q, J=12.58 Hz, 2H), 2.77 (t, J=4.55 Hz, 4H), 2.65 (t, J=6.35 Hz, 2H), 2.48 (m, 6H), 2.27 (s, 3H), 2.21 (s, 3H)

Example 62

Synthesis of 1-N-[2-[4-(2,4-dimethylphenyl)piperazin-1-yl]ethyl]carbamoylethyl-2-phenylimidazole [Compound No. 62]

Yield 37.66%
$^1$H NMR (300 MHz, CDCl$_3$) δ 7.61 (m, 2H), 7.44 (m, 3H), 7.10 (s, 1H), 7.07 (s, 1H), 6.98 (m, 3H), 6.34 (br, 1H), 4.40 (t, J=6.75 Hz, 2H), 3.35 (q, J=10.87 Hz, 2H), 2.89 (t, J=4.28 Hz, 2H), 2.54 (m, 10H), 2.28 (s, 3H), 2.23 (s, 3H)

Example 63

Synthesis of 1-N-{2-[4-(4-chlorophenyl) (phenyl)methylpiperazin-1-yl]ethyl}carbamoylethyl-2-phenylimidazole [Compound No. 63]

Yield 38.44%
$^1$H NMR (300 MHz, CDCl$_3$) δ 7.57 (m, 2H), 7.42 (m, 3H), 7.33 (m, 9H), 7.07 (s, 1H), 7.04 (s, 1H), 6.22 (br, 1H), 4.36 (t, J=6.78 Hz, 2H), 4.22 (s, 1H), 3.28 (q, J=11.18 Hz, 2H), 2.48 (m, 12H)

Example 64

Synthesis of 1-N-[2-[4-(4-chlorophenyl)(phenyl)methylpiperazin-1-yl]ethyl]carbamoylethyl-4-phenylimidazole [Compound No. 64]

Yield 35.29%
$^1$H NMR (300 MHz, CDCl$_3$) δ 7.72 (s, 1H), 7.69 (s, 1H), 7.49 (s, 1H), 7.24 (m, 13H), 6.53 (br, 1H), 4.30 (t, J=6.18 Hz, 2H), 4.11 (s, 1H), 3.33 (q, J=11.00 Hz, 2H), 2.64 (t, J=6.31 Hz, 2H), 2.44 (m, 6H), 2.28 (br, 4H)

Example 65

Synthesis of 1-N-[2-[4-(2-fluorobenzyl)piperazin-1-yl]ethyl]carbamoylethyl-2-phenylimidazole [Compound No. 65]

Yield 52.00%
$^1$H NMR (300 MHz, CDCl$_3$) δ 7.54 (m, 2H), 7.40 (m, 4H), 7.20 (m, 1H), 7.08 (m, 4H), 6.45 (br, 1H), 4.32 (t, J=6.81 Hz, 2H), 3.58 (s, 2H), 3.24 (q, J=5.52 Hz, 2H), 2.39 (m, 12H)

Example 66

Synthesis of 1-N-{2-[4-(2-fluorobenzyl)piperazin-1-yl]ethyl}carbamoylethyl-4-phenylimidazole [Compound No. 66]

Yield 50.00%
$^1$H NMR (300 MHz, CDCl$_3$) δ 7.74 (d, J=1.11 Hz, 2H), 7.44 (s, 1H), 7.29 (m, 6H), 7.10 (m, 2H), 6.46 (br, 1H), 4.26 (t, J=6.15 Hz, 2H), 3.50 (s, 1H), 3.27 (q, J=5.52 Hz, 2H), 2.58 (t, J=6.27 Hz, 2H), 2.36 (m, 10H)

Example 67

Synthesis of 1-N-[2-[4-(3-methylbenzyl)piperazin-1-yl]ethyl]carbamoylethyl-4-phenylimidazole 의 [Compound No. 67]

Yield 32.00%
$^1$H NMR (300 MHz, CDCl$_3$) δ 7.75 (d, J=7.30 Hz, 2H), 7.51 (s, 1H), 7.34 (t, J=7.42 Hz, 2H), 7.28 (s, 1H), 7.19 (t, J=2.36 Hz, 2H), 7.17 (m, 3H), 6.83 (br, 1H), 4.30 (t, J=6.15 Hz, 2H), 3.38 (s, 2H), 3.33 (t, J=5.58 Hz, 2H), 2.66 (t, J=6.28 Hz, 2H), 2.47 (m, 6H), 2.40 (br, 4H), 2.34 (s, 3H)

Example 68

Synthesis of 1-N-[2-[4-(3-methylbenzyl)piperazin-1-yl]ethyl]carbamoylethyl-2-phenylimidazole [Compound No. 68]

Yield 57.00%
$^1$H NMR (300 MHz, CDCl$_3$) δ 7.58 (m, 2H), 7.43 (m, 3H), 7.20 (m, 1H), 7.06 (m, 5H), 6.49 (br, 1H), 4.35 (t, J=6.77 Hz, 2H), 3.48 (s, 2H), 3.29 (q, J=5.63 Hz, 2H), 2.50 (m, 12H), 2.34 (s, 3H)

Example 69

Synthesis of 1-N-[2-[4-(4-fluorobenzyl)piperazin-1-yl]ethyl]carbamoylethyl-2-phenylimidazole [Compound No. 69]

Yield 69.40%
$^1$H NMR (300 MHz, CDCl$_3$) δ 7.52 (s, 2H), 7.43 (d, J=2.55 Hz, 3H), 7.23 (m, 2H), 7.03 (m, 4H), 6.63 (br, 1H), 4.33 (t, J=6.78 Hz, 2H), 3.45 (s, 2H), 3.27 (q, J=5.79 Hz, 2H), 2.40 (m, 12H)

Example 70

Synthesis of 1-N-[2-[4-(4-fluorobenzyl)piperazin-1-yl]ethyl]carbamoylethyl-4-phenylimidazole [Compound No. 70]

Yield 75.95%
$^1$H NMR (300 MHz, CDCl$_3$) δ 7.74 (d, J=1.14 Hz, 2H), 7.48 (s, 1H), 7.34 (t, J=7.38 Hz, 2H), 7.22 (m, 3H), 6.97 (m, 3H), 6.46 (br, 1H), 4.29 (t, J=6.18 Hz, 2H), 3.31 (s, 2H), 3.28 (q, J=5.70 Hz, 2H), 2.60 (t, J=6.33 Hz, 6H), 2.35 (m, 6H)

Example 71

Synthesis of 1-N-[2-(4-phenylpiperazin-1-yl)ethyl]carbamoylethyl-4-phenylimidazole [Compound No. 71]

Yield 36.37%
$^1$H NMR (300 MHz, CDCl$_3$) δ 7.77 (d, J=1.32 Hz, 2H), 7.46 (s, 1H), 7.36 (t, J=7.35 Hz, 2H), 7.24 (t, J=6.00 Hz, 4H), 6.85 (q, J=7.94 Hz, 3H), 6.43 (br, 1H), 4.28 (t, J=6.17 Hz, 2H), 3.33 (q, J=5.64 Hz, 2H), 3.01 (t, J=4.77 Hz, 4H), 2.59 (t, J=6.32 Hz, 2H), 2.41-2.48 (m, 6H)

Example 72

Synthesis of 1-N-[2-(4-phenylpiperazin-1-yl)ethyl]carbamoylethyl-2-phenylimidazole [Compound No. 72]

Yield 52.79%
$^1$H NMR (300 MHz, CDCl$_3$) δ 7.57 (d, J=1.85 Hz, 2H), 7.41-7.55 (m, 3H), 7.27 (t, J=7.29 Hz, 2H), 7.08 (s, 1H), 7.04 (s, 1H), 6.87-6.94 (m, 3H), 6.33 (br, 1H), 4.37 (t, J=6.77 Hz, 2H), 3.32 (q, J=5.60 Hz, 2H), 3.10 (t, J=4.77 Hz, 4H), 2.57 (t, J=5.03 Hz, 4H), 2.44-2.52 (m, 4H)

Example 73

Synthesis of 1-N-[2-[4-(4-fluorophenyl)piperazin-1-yl]ethyl]carbamoylethyl-4-phenylimidazole [Compound No. 73]

Yield 59.31%
$^1$H NMR (300 MHz, CDCl$_3$) δ 7.76 (d, J=7.11 Hz, 2H), 7.48 (s, 1H), 7.35 (t, J=7.31 Hz, 2H), 7.22-7.24 (m, 1H), 6.88-6.95 (m, 3H), 6.69-6.73 (m, 2H), 6.43 (br, 1H), 4.29 (t, J=6.05 Hz, 2H), 3.33 (q, J=5.75 Hz, 2H), 2.93 (t, J=4.75 Hz, 4H), 2.61 (t, J=5.99 Hz, 2H), 2.43-2.49 (m, 6H)

Example 74

Synthesis of 1-N-[2-[4-(4-fluorophenyl)piperazin-1-yl]ethyl]carbamoylethyl-2-phenylimidazole [Compound No. 74]

Yield 82.44%
$^1$H NMR (300 MHz, CDCl$_3$) δ 7.54 (d, J=5.28 Hz, 2H), 7.41 (d, J=6.92 Hz, 3H), 7.05 (s, 1H), 6.94 (t, J=8.34 Hz, 3H), 6.82-6.87 (m, 2H), 6.56 (br, 1H), 4.34 (t, J=6.66 Hz, 2H), 3.32 (q, J=5.62 Hz, 2H), 3.08 (t, J=4.64 Hz, 4H), 2.58 (t, J=4.85 Hz, 4H), 2.45-2.51 (m, 4H)

Example 75

Synthesis of 1-N-[2-[4-(4-methoxyphenyl)piperazin-1-yl]ethyl]carbamoylethyl-4-phenylimidazole [Compound No. 75]

Yield 47.30%
$^1$H NMR (300 MHz, CDCl$_3$) δ 7.76 (d, J=7.14 Hz, 2H), 7.48 (s, 1H), 7.35 (t, J=7.31 Hz, 2H), 7.22-7.27 (m, 2H), 6.74-6.82 (m, 4H), 6.50 (br, 1H), 4.29 (t, J=6.02 Hz, 2H), 3.76 (s, 3H), 3.34 (q, J=5.69 Hz, 2H), 2.93 (t, J=4.70 Hz, 4H), 2.62 (t, J=6.22 Hz, 2H), 2.44-2.53 (m, 6H)

Example 76

Synthesis of 1-N-[2-[4-(4-methoxyphenyl)piperazin-1-yl]ethyl]carbamoylethyl-2-phenylimidazole [Compound No. 76]

Yield 49.60%
$^1$H NMR (300 MHz, CDCl$_3$) δ 7.58 (d, J=6.14 Hz, 2H), 7.42 (d, J=3.82 Hz, 3H), 7.07 (s, 2H), 6.82-6.90 (m, 4H), 6.50 (br, 1H), 4.36 (t, J=6.74 Hz, 2H), 3.77 (s, 3H), 3.35 (q, J=5.75 Hz, 2H), 3.09 (t, J=4.69 Hz, 4H), 2.63 (t, 4.95 Hz, 4H), 2.50-2.55 (m, 4H)

Example 77

Synthesis of 1-N-[2-[4-(2-fluorophenyl)piperazin-1-yl]ethyl]carbamoylethyl-4-phenylimidazole [Compound No. 77]

Yield 53.38%
$^1$H NMR (300 MHz, CDCl$_3$) δ 7.75 (d, J=7.11 Hz, 2H), 7.46 (s, 1H), 7.34 (t, J=7.34 Hz, 2H), 7.22 (t, J=1.20 Hz, 2H), 6.92-7.01 (m, 2H), 6.48 (br, 1H), 4.28 (t, J=6.35 Hz, 2H), 3.32 (q, J=5.66 Hz, 2H), 2.93 (t, J=4.37 Hz, 4H), 2.60 (t, J=6.26 Hz, 2H), 2.51 (t, J=4.64 Hz, 4H), 2.45 (t, J=6.00 Hz, 2H)

Example 78

Synthesis of N-{2-[4-(2-fluorophenyl)piperazin-1-yl]ethyl}carbamoylethyl-(2-phenyl)imidazole [Compound No. 78]

Yield 47.45%
$^1$H NMR (300 MHz, CDCl$_3$) δ 7.53 (d, J=4.32 Hz, 2H), 7.40-7.42 (m, 3H), 7.02 (q, J=6.80 Hz, 4H), 6.91-6.92 (m, 2H), 6.61 (br, 1H), 4.34 (t, J=6.79 Hz, 2H), 3.33 (q, J=5.55 Hz, 2H), 3.07 (t, J=4.37 Hz, 4H), 2.60 (t, J=4.63 Hz, 4H), 2.47-2.52 (m, 4H)

Example 79

Synthesis of 1-N-[2-[4-(3-chlorophenyl)piperazin-1-yl]ethyl]carbamoylethyl-4-phenylimidazole [Compound No. 79]

Yield 46.23%
$^1$H NMR (300 MHz, CDCl$_3$) δ 7.75 (d, J=7.63 Hz, 2H), 7.45 (s, 1H), 7.36 (t, J=7.47 Hz, 2H), 7.24 (t, J=7.23 Hz, 2H), 7.12 (t, J=8.15 Hz, 1H), 6.77 (t, J=7.86 Hz, 2H), 6.63 (d, J=8.27 Hz, 1H), 6.38 (br, 1H), 4.28 (t, J=6.12 Hz, 2H), 3.32 (q, J=5.42 Hz, 2H), 2.95-2.97 (m, 4H), 2.59 (t, J=5.79 Hz, 2H), 2.41 (t, J=4.79 Hz, 6H)

Example 80

Synthesis of 1-N-[2-[4-(3-chlorophenyl)piperazin-1-yl]ethyl]carbamoylethyl-2-phenylimidazole [Compound No. 80]

Yield 63.36%
$^1$H NMR (300 MHz, CDCl$_3$) δ 7.55 (d, J=4.36 Hz, 2H), 7.41-7.44 (m, 3H), 7.15-7.16 (m, 1H), 7.05 (d, J=9.67 Hz, 2H), 6.71-6.85 (m, 3H), 6.36 (br, 1H), 4.36 (t, J=6.74 Hz, 2H), 3.32 (q, J=5.68 Hz, 2H), 3.15 (t, J=4.78 Hz, 4H), 2.39-2.56 (m, 8H)

Example 81

Synthesis of 1-N-[2-[4-(2,3-dimethylphenyl)piperazin-1-yl]ethyl]carbamoylethyl-2-phenylimidazole [Compound No. 81]

Yield 60.83%
$^1$H NMR (300 MHz, CDCl$_3$) δ 7.59 (d, J=6.31 Hz, 2H), 7.42-7.48 (m, 3H), 7.06-7.11 (m, 3H), 6.91 (d, J=7.70 Hz, 2H), 6.29 (br, 1H), 4.39 (t, J=6.79 Hz, 2H), 3.34 (q, J=5.62 Hz, 2H), 2.88 (t, J=4.29 Hz, 4H), 2.47-2.58 (m, 8H), 2.27 (s, 3H), 2.21 (s, 3H)

Example 82

Synthesis of 1-N-[2-(4-diphenylmethylpiperazin-1-yl)ethyl]carbamoylethyl-4-phenylimidazole [Compound No. 82]

Yield 25.82%
$^1$H NMR (300 MHz, CDCl$_3$) δ 7.56 (d, J=1.63 Hz, 2H), 7.42 (t, J=7.07 Hz, 7H), 7.28 (t, J=7.13 Hz, 4H), 7.20 (d, J=7.19 Hz, 1H), 7.05 (d, J=10.04 Hz, 1H), 6.18 (br, 1H), 4.36 (t, J=6.80 Hz, 2H), 4.24 (s, 1H), 3.28 (q, J=5.63 Hz, 2H), 2.40-2.52 (m, 12H)

Example 83

Synthesis of 1-N-[2-(4-benzylpiperazin-1-yl)ethyl]carbamoylethyl-2-phenylimidazole [Compound No. 83]

Yield 33.51%
$^1$H NMR (300 MHz, CDCl$_3$) δ 7.51-7.54 (m, 2H), 7.39-7.44 (m, 3H), 7.25-7.29 (m, 5H), 7.02-7.03 (m, 2H), 6.65 (br, 1H), 4.32 (t, J=6.81 Hz, 2H), 3.49 (s, 2H), 3.25 (q, J=5.85, 2H), 2.37-2.50 (m, 12H)

Example 84

Synthesis of 1-N-[2-(4-benzylpiperazin-1-yl)ethyl]carbamoylethyl-4-phenylimidazole [Compound No. 84]

Yield 30.21%
$^1$H NMR (300 MHz, CDCl$_3$) δ 7.71 (d, J=7.08 Hz, 2H), 7.20-7.33 (m, 10H), 6.64 (br, 1H), 4.25 (t, J=6.09 Hz, 2H), 3.41 (s, 2H), 3.28 (q, J=5.61 Hz, 2H), 2.58 (t, J=6.24 Hz, 2H), 2.34-2.38 (m, 10H)

Example 85

Synthesis of 1-N-[2-(4-phenylpiperazin-1-yl)ethyl]carbamoylethyl-2-methylimidazole [Compound No. 85]

Yield 81.17%
$^1$H NMR (300 MHz, CDCl$_3$) δ 7.27 (t, J=2.01 Hz, 2H), 6.89 (t, J=8.58 Hz, 2H), 6.82-6.85 (m, 3H), 6.49 (br, 1H), 4.17 (t, 6.51, 2H), 3.33 (q, J=5.61 Hz, 2H), 3.15 (t, J=4.65 Hz, 4H), 2.52-2.57 (m, 6H), 2.46 (t, J=5.88 Hz, 2H), 2.34 (s, 3H)

Example 86

Synthesis of 1-N-[2-(4-phenylpiperazin-1-yl)ethyl]carbamoylethyl-4-methylimidazole [Compound No. 86]

Yield 68.62%
$^1$H NMR (300 MHz, CDCl$_3$) δ 7.32-7.38 (m, 1H), 7.25 (t, J=5.13 Hz, 2H), 6.85-6.92 (m, 3H), 6.72 (s, 1H), 6.62 (br, 1H), 4.17 (t, J=6.57 Hz, 2H), 3.33-3.42 (m, 2H), 3.15 (t, J=4.89 Hz, 4H), 2.56 (t, J=6.15 Hz, 6H), 2.46 (t, J=5.46 Hz, 2H), 2.17 (d, J=4.65 Hz, 3H)

Example 87

Synthesis of 1-N-[2-[4-(4-fluorophenyl)piperazin-1-yl]ethyl]carbamoylethyl-4-methylimidazole [Compound No. 87]

Yield 67.06%
$^1$H NMR (300 MHz, CDCl$_3$) δ 7.26-7.33 (m, 1H), 6.87 (t, J=6.85 Hz, 2H), 6.75-6.80 (m, 2H), 6.58 (d, J=11.95 Hz, 1H), 4.09 (q, J=6.79 Hz, 2H), 3.25-3.30 (m, 2H), 3.00 (t, J=4.60 Hz, 4H), 2.50 (t, J=6.42 Hz, 6H), 2.39 (t, J=6.06 Hz, 2H), 2.08 (d, J=10.61 Hz, 3H)

Example 88

Synthesis of 1-N-{2-[4-(4-fluorophenyl)piperazin-1-yl]ethyl}carbamoylethyl-2-methylimidazole [Compound No. 88]

Yield 51.59%
$^1$H NMR (300 MHz, CDCl$_3$) δ 6.91 (t, J=6.13 Hz, 2H), 6.79-6.84 (m, 4H), 6.72 (br, 1H), 4.13 (t, J=6.56 Hz, 2H), 3.29 (t, J=5.66 Hz, 2H), 3.04 (t, J=4.77 Hz, 4H), 2.49-2.55 (m, 6H), 2.43 (t, J=6.02 Hz, 2H), 2.29 (s, 3H)

Example 89

Synthesis of 1-N-[2-[4-(4-fluorobenzyl)piperazin-1-yl]ethyl]carbamoylethyl-2-methylimidazole [Compound No. 89]

Yield 20.31%
$^1$H NMR (300 MHz, CDCl$_3$) δ 7.23-7.27 (m, 2H), 6.98 (t, J=6.69 Hz, 2H), 6.82 (s, 2H), 6.40 (br, 1H), 4.17 (t, J=6.54 Hz, 2H), 3.45 (s, 2H), 3.28 (q, J=5.58 Hz, 2H), 2.79 (br, 2H), 2.53 (t, J=6.60 Hz, 2H), 2.34-2.42 (m, 8H), 2.32 (s, 3H)

Example 90

Synthesis of 1-N-{2-[4-(4-fluorobenzyl)piperazin-1-yl]ethyl}carbamoylethyl-4-methylimidazole [Compound No. 90]

Yield 47.55%
$^1$H NMR (300 MHz, CDCl$_3$) δ 7.33-7.39 (m, 1H), 7.25 (q, J=2.61 Hz, 2H), 6.98 (t, J=8.40 Hz, 2H), 6.61-6.69 (m, 1H), 6.41 (br, 1H), 4.19 (q, J=7.65 Hz, 2H), 3.45 (s, 2H), 3.30 (q, J=2.55 Hz, 2H), 2.67 (s, 2H), 2.52-2.58 (m, 2H), 2.38-2.42 (m, 8H), 2.17 (d, J=, 9.33 Hz, 3H)

Example 91

Synthesis of 1-N-[2-[4-(2-fluorophenyl)piperazin-1-yl]ethyl]carbamoylethyl-2-methylimidazole [Compound No. 91]

Yield 40.08%
$^1$H NMR (300 MHz, CDCl$_3$) δ 7.00 (q, J=1.80 Hz, 2H), 6.82-6.95 (m, 2H), 6.81 (s, 1H), 6.70 (br, 1H), 4.16 (t, J=6.60 Hz, 2H), 3.33 (q, J=5.67 Hz, 2H), 3.05 (t, J=4.41 Hz, 4H), 2.51-2.58 (m, 6H), 2.46 (t, J=6.00 Hz, 2H), 2.32 (s, 3H)

Example 92

Synthesis of 1-N-[2-[4-(2-fluorophenyl)piperazin-1-yl]ethyl]carbamoylethyl-4-methylimidazole [Compound No. 92]

Yield 30.16%
$^1$H NMR (300 MHz, CDCl$_3$) δ 7.03 (d, J=1.14 Hz, 1H), 6.91-7.03 (m, 4H), 6.59-6.62 (m, 2H), 4.17 (q, J=6.57 Hz, 2H), 3.33 (t, J=0.87 Hz, 2H), 3.04-3.07 (m, 6H), 2.54-2.59 (m, 4H), 2.48 (t, J=6.09 Hz, 2H), 2.15 (d, J=2.22 Hz, 3H)

Example 93

Synthesis of 1-N-[2-[4-(4-chlorophenyl) (phenyl)methylpiperazin-1-yl]ethyl]carbamoylethyl-2-methylimidazole [Compound No. 93]

Yield 30.04%
$^1$H NMR (300 MHz, CDCl$_3$) δ 7.33-7.36 (m, 4H), 7.19-7.30 (m, 5H), 6.82 (d, J=3.11 Hz, 2H), 6.22 (br, 1H), 4.13-4.22 (m, 3H), 3.27 (q, J=5.67 Hz, 2H), 2.52 (t, J=6.65 Hz, 4H), 2.41 (t, J=5.91 Hz, 6H), 2.35 (s, 3H), 2.34 (s, 2H)

Example 94

Synthesis of 1-N-[2-[4-(4-chlorophenyl) (phenyl)methylpiperazin-1-yl]ethyl]carbamoylethyl-4-methylimidazole [Compound No. 94]

Yield 29.20%
$^1$H NMR (300 MHz, CDCl$_3$) δ 7.29-7.36 (m, 5H), 7.22-7.27 (m, 5H), 6.61-6.67 (m, 1H), 6.20 (br, 1H), 4.14-4.22 (m, 3H), 3.45 (t, J=6.08 Hz, 2H), 3.30 (br, 2H), 2.54 (q, J=3.61 Hz, 2H), 2.34-2.44 (m, 8H), 2.18 (d, J=2.24 Hz, 2H), 2.15 (s, 1H), 2.10 (s, 2H)

Example 95

Synthesis of 1-N-[2-[4-benzylpiperazin-1-yl]ethyl]carbamoylethyl-4-methylimidazole [Compound No. 95]

Yield 57.43%
$^1$H NMR (300 MHz, CDCl$_3$) δ 7.23-7.30 (m, 5H), 6.68 (s, 1H), 4.16 (q, J=7.83 Hz, 2H), 3.48 (s, 2H), 3.25-3.29 (m, 2H), 3.08 (br, 2H), 2.51-2.57 (m, 2H), 2.37-2.42 (m, 8H), 2.14-2.17 (m, 3H)

Example 96

Synthesis of 1-N-[2-(4-diphenylmethylpiperazin-1-yl)ethyl]carbamoylethyl-2-methylimidazole [Compound No. 96]

Yield 8.29%
$^1$H NMR (300 MHz, CDCl$_3$) δ 7.40 (d, J=7.55 Hz, 4H), 7.26-7.31 (m, 4H), 7.17-7.22 (m, 2H), 6.81-6.86 (m, 2H), 6.63 (br, 1H), 4.24 (s, 1H), 4.13 (t, J=4.43 Hz, 2H), 3.44-3.45 (m, 6H), 2.53 (t, J=6.63 Hz, 2H), 2.30-2.34 (m, 9H)

Example 97

Synthesis of 1-N-[2-[4-(4-methoxybenzyl)piperazin-1-yl]ethyl]carbamoylethyl-4-methylimidazole [Compound No. 97]

Yield 45.38%
$^1$H NMR (300 MHz, CDCl$_3$) δ 7.31-7.37 (m, 1H), 6.79-6.88 (m, 4H), 6.55-6.61 (m, 1H), 6.50 (br, 1H), 4.18 (t, J=6.51

Hz, 2H), 3.75 (s, 3H), 3.32-3.34 (m, 2H), 3.02-3.05 (m, 4H), 2.55 (m, 6H), 2.45 (t, J=5.37 Hz, 2H), 2.15-2.19 (m, 3H)

Example 98

Synthesis of 1-N-{2-[4-(4-methoxybenzyl)piperazin-1-yl]ethyl}carbamoylethyl-2-methylimidazole [Compound No. 98]

Yield 68.85%
$^1$H NMR (300 MHz, CDCl$_3$) δ 6.96 (br, 1H), 6.75-6.85 (m, 6H), 4.11 (t, J=6.69 Hz, 2H), 3.70 (s, 3H), 3.29 (t, J=5.71 Hz, 2H), 3.00 (t, J=4.17 Hz, 4H), 2.48-2.54 (m, 6H), 2.42 (t, J=6.03 Hz, 2H), 2.28 (s, 3H)

Example 99

Synthesis of 1-N-{2-[4-(3,4-dichlorobenzyl)piperazin-1-yl]ethyl}carbamoylethyl-2-methylimidazole [Compound No. 99]

Yield 31.76%
$^1$H NMR (300 MHz, CDCl$_3$) δ 7.38-7.44 (m, 2H), 7.28 (s, 1H), 7.14-7.17 (m, 1H), 6.83-6.87 (m, 1H), 6.45 (br, 1H), 4.14-4.21 (m, 4H), 3.46 (s, 6H), 2.55 (t, J=6.59 Hz, 2H), 2.32-2.40 (m, 9H)

Example 100

Synthesis of 1-N-[2-[4-(3,4-dichlorobenzyl)piperazin-1-yl]ethyl]carbamoylethyl-4-methylimidazole [Compound No. 100]

Yield 23.65%
$^1$H NMR (300 MHz, CDCl$_3$) δ 7.33-7.40 (m, 3H), 7.15 (d, J=7.09 Hz, 1H), 6.61-6.69 (m, 1H), 6.40 (br, 1H), 4.18 (q, J=7.62 Hz, 2H), 3.43 (br, 2H), 2.75 (br, 2H), 2.52-2.58 (m, 2H), 2.39-2.41 (m, 10H), 2.16-2.19 (m, 3H)

Example 101

Synthesis of 1-N-[2-[4-(4-chlorobenzyl)piperazin-1-yl]ethyl]carbamoylethyl-2-methylimidazole [Compound No. 101]

Yield 9.12%
$^1$H NMR (300 MHz, CDCl$_3$) δ 7.23-7.30 (m, 4H), 6.87 (s, 1H), 6.84 (s, 1H), 6.12 (br, 1H), 4.20 (t, J=6.60 Hz, 2H), 3.48 (s, 1H), 3.29 (q, J=5.69 Hz, 1H), 2.55 (t, J=6.60 Hz, 2H), 2.39-2.43 (m, 10H), 2.04 (s, 3H)

Example 102

Synthesis of 1-N-[2-[4-(4-chlorobenzyl)piperazin-1-yl]ethyl]carbamoylethyl-4-methylimidazole [Compound No. 102]

Yield 12.82%
$^1$H NMR (300 MHz, CDCl$_3$) δ 7.36-7.40 (m, 1H), 7.22-7.30 (m, 4H), 6.63-6.72 (m, 1H), 6.18 (br, 1H), 4.17-4.24 (m, 2H), 3.47 (s, 2H), 3.30 (br, 2H), 2.53-2.59 (m, 2H), 2.40-2.43 (m, 10H), 2.20 (d, J=7.94 Hz, 3H)

Example 103

Synthesis of 1-N-[2-[4-(3-chlorophenyl)piperazin-1-yl]ethyl]carbamoylethyl-2-methylimidazole [Compound No. 103]

Yield 31.20%
$^1$H NMR (300 MHz, CDCl$_3$) δ 7.13-7.18 (m, 1H), 6.83-6.85 (m, 4H), 6.76-6.82 (m, 1H), 6.35 (br, 1H), 4.19 (t, I=6.51 Hz, 2H), 2.32 (t, J=5.79 Hz, 2H), 3.15 (t, J=4.92 Hz, 4H), 2.52-2.57 (m, 6H), 2.46 (t, J=6.06 Hz, 2H), 2.35 (s, 3H)

Example 104

Synthesis of 1-N-{2-[4-(3-chlorophenyl)piperazin-1-yl]ethyl}carbamoylethyl-4-methylimidazole [Compound No. 104]

Yield 25.59%
$^1$H NMR (300 MHz, CDCl$_3$) δ 7.33-7.38 (m, 1H), 7.13 (t, J=3.93 Hz, 1H), 6.74-6.85 (m, 3H), 6.62-6.71 (m, 1H), 6.30 (br, 1H), 4.21 (t, J=6.69 Hz, 2H), 3.32-3.35 (m, 2H), 3.13-3.16 (m, 4H), 2.53-2.58 (m, 6H), 2.46 (t, J=5.97 Hz, 2H), 2.17-2.19 (m, 3H)

Example 105

Synthesis of 1-N-[2-[4-diphenylmethylpiperazin-1-yl]ethyl]carbamoylethyl-4-methylimidazole [Compound No. 105]

Yield 40.74%
$^1$H NMR (300 MHz, CDCl$_3$) δ 7.37-7.41 (m, 4H), 7.25-7.28 (m, 4H), 7.17-7.22 (m, 2H), 6.81-6.84 (m, 2H), 6.60 (br, 1H), 4.24 (s, 1H), 4.21 (t, J=4.45 Hz, 2H), 3.44-3.45 (m, 6H), 2.53 (t, J=6.63 Hz, 2H), 2.30-2.34 (m, 6H), 2.16-2.19 (m, 3H)

Formulation Examples

The novel compounds represented by the formula 1 according to the present invention can be prepared in various formulations. The followings illustrate a few of the methods of formulations which comprise the compounds represented by the formula 1 as active ingredient, however, the present invention shall not be construed as limiting the scope by the same.

Formulation 1: Tablets (Direct Pressure)
After sieving 5.0 mg of active ingredient, it was mixed with 14.1 mg of lactose, 0.8 mg of USNF Crospovidone, and 0.1 mg of magnesium stearate and pressed to prepare a tablet.

Formulation 2: Tablets (Wet Granulation)
After sieving 5.0 mg of active ingredient, it was mixed with 16.0 mg of lactose, and 4.0 mg of starch. After dissolving 0.3 mg of polysorbate 80 in water, an adequate amount of the same was micronized. The micronized resultant was dried, sieved and then mixed with 2.7 mg of colloidal silicon dioxide and 2.0 mg of magnesium stearate. The micronized resultant was pressed to form a tablet.

Formulation 3: Powders and Capsules After sieving 5.0 mg of active ingredient, it was mixed with 14.8 mg of lactose, 10.0 mg of polyvinyl pyrrolidone and 0.2 mg of magnesium stearate. The mixture was filled into a hard No. 5 capsule using a suitable apparatus.

Formulation 4: Injections
An injection comprising 100 mg of active ingredient, 180 mg of mannitol, 26 mg of Na$_2$HPO$_4$.12H$_2$O and 2,974 mg of distilled water was prepared.

[Efficacy Test]

Experimental Example

Test of Antagonistic Activity Against T-Type Calcium Channels

The novel compounds of the present invention presented as the formula 1 were tested for their antagonistic activities against T-type calcium channels using the methods described below. More specifically, the synthesized compounds were screened as follows: First, as a primary screening, the compounds having 40% or higher of antagonistic activities against T-type calcium channels were selected using the FDSS6000, a high throughput screening (HTS) device. Then, as a secondary screening, the $IC_{50}$ (effective inhibitory concentration) values were obtained using the electrophysiological methods.

1) Methods for the Measurements of T-Type Calcium Channel Activity Using the FDSS6000

12 to 24 hours prior to the FDSS-based HTS assay, HEK293 cells stably expressing both $\alpha_{1G}$ T-type calcium channels and Kir2.1 channels ($\alpha_{1G}$ cell line: KCTC 10519BP, KRIBB (Korea Research Institute of Bioscience and Biotechnology) (GENE BANK) were seeded onto the 96-well plate coated with poly-L-lysine (0.05 mg/mL) at a density of $4\times10^4$ cells/well using a cell distributor (Titertek, USA). On the following day, the cells attached onto the 96-well plate were washed three times with a HEPES-buffered solution (150 mM NaCl, 5 mM KCl, 1 mM $MgCl_2$, 2 mM $CaCl_2$, 10 mM HEPES, 10 mM glucose, and pH 7.4) using an automatic 96-well plate washer (BioTek, USA), and then labeled with a fluorescent calcium indicator dye, Fluo-3/AM (5 µM) and 0.001% Pluronic F-127 in a HEPES-buffered solution at room temperature for 1 hour and then washed again with a HEPES-buffered solution twice. 10 minutes prior to the FDSS6000 measurements, the cells was washed with a HEPES-buffered solution containing 10 mM $CaCl_2$ once and the final volume was adjusted.

In addition to the 96-well plates with cells, the two drug plates were prepared: one containing KCl (final concentration of 75 mM) for the activation of T-type calcium channels, and the other containing testing compounds (blocking agents of T-type calcium channels). Since most cell-based HTS devices are provided with a liquid application system for drug injection but not with a liquid absorption system, the KCl solution and the blocking agents for screening were prepared at concentrations five times higher than the final concentrations in the 10 mM $CaCl_2$ HEPES-buffered solution, and then diluted in the cell plate, and the activities were measured. The specific method of the FDSS6000 measurements is as follows: For the FDSS6000 measurements, after the 20-sec baseline recordings, cells were preincubated with drugs for 75 seconds and the change in intracellular calcium concentration induced by KCl was measured. The percent inhibition by a test compound was calculated as integrated values of 340/380 fluorescent ratio of untreated and drug-treated cells. The control drug was 10 µM of Mibefradil®.

In details, cells were selectively exposed to 340 nm and 380 nm light excited by 4 xenon lamps installed in FDSS6000 using a computer-controlled filter wheel. The emitter fluorescence light through a 515 nm long-pass filter was passed by a freezing digital CCD camera mounted on the device. Data were collected every 1.23 seconds, and an average value of $^{340}/_{380}$ fluorescent ratio for each well was obtained using a digital fluorescent analyzer. Data acquisition and analysis were performed using a program provided by Hamamatsu Photonics.

2) Methods for the Measurements of T-Type Calcium Channel Activity Using an Electrophysiological Whole-Cell Patch-Clamp Technique HEK293 cells stably expressing T-type calcium channels were cultured in DMEM (Dulbecco's modified Eagle's medium) containing 10% (v/v) fetal bovine serum and 1% penicillin/streptomycin (v/v) in humidified 5% $CO_2$ at 36.5° C. Cells expressing $\alpha_{1G}$ T-type calcium channels were selected using G-418 (0.5 mg/mL) in the culture medium. The culture medium was replaced with a fresh one every 3-4 days, and cells were subcultured every week.

Cells were seeded onto the coverglass coated with poly-L-lysine (0.5 mg/mL) for the measurements of T-type calcium channel activity 2-7 days prior to the recordings. Whole-cell recordings of T-type calcium channel currents were performed using an EPC-9 patch clamp amplifier (HEKA, Germany). Whole-cell currents were recorded using micropipettes with resistance of 3-4 MΩ with the pipette (intracellular) solution containing (in mM): 130 KCl, 11 EGTA, 5 Mg-ATP, and 10 HEPES, pH to 7.4 and with the bath (extracellular) solution containing (in mM): 140 NaCl, 2 $CaCl_2$, and 10 HEPES, pH to 7.4. The inward currents of T-type calcium channels were evoked by the test pulses of −30 mV for 50 ms at a holding potential of −100 mV every 10 seconds.

Each compound was dissolved in dimethylsulfoxide (DMSO) as 10 mM stock solutions and diluted in the bath solution to 10 µM (containing 0.1% DMSO). The initial test was performed to find the range of drug concentrations that exhibits the inhibition effects, in which the $IC_{50}$ values were obtained (mostly in the range of 0.1-100 µM). More specifically, each compound was perfused to the bath for about 30-60 seconds, and the inhibition of the inward peak currents by a test compound was calculated as a percent inhibition from which the $IC_{50}$ values were determined. The results are shown in the Table 2.

TABLE 2

| Test Compound | FDSS (%, 10 µM) | HEK293 (%, 100 µM) | $IC_{50}$ (µM) |
|---|---|---|---|
| Compound No. 2 | 33.47 | NT | NT |
| Compound No. 3 | 55.49 | 64.7 ± 2.2 | 4.89 ± 0.44 |
| Compound No. 5 | 64.67 | 86.5 ± 1.8 | 3.00 ± 0.26 |
| Compound No. 15 | 34.38 | NT | NT |
| Compound No. 16 | 34.28 | NT | NT |
| Compound No. 18 | 39.30 | 50.0 ± 0.6 | 9.36 ± 0.65 |
| Compound No. 21 | 36.75 | NT | NT |
| Compound No. 23 | 23.43 | NT | NT |
| Compound No. 13 | 54.74 | 71.1 ± 3.3 | 3.67 ± 0.23 |
| Compound No. 20 | 45.22 | 22.9 ± 1.4 | 22.28 ± 1.46 |
| Compound No. 25 | 63.68 | 74.3 ± 1.3 | 4.35 ± 0.14 |
| Compound No. 26 | 35.12 | NT | NT |
| Compound No. 27 | 37.79 | NT | NT |
| Compound No. 35 | 34.99 | NT | NT |
| Compound No. 38 | 33.78 | NT | NT |
| Compound No. 45 | 47.90 | 64.7 ± 2.2 | 5.46 ± 0.57 |
| Compound No. 46 | 51.94 | 67.6 ± 1.3 | 4.97 ± 0.18 |
| Compound No. 53 | 42.25 | — | 0.00046 ± 0.00 |
| Compound No. 54 | 24.25 | NT | NT |
| Compound No. 55 | 49.63 | 51.9 ± 0.1 | 8.66 ± 0.12 |
| Compound No. 56 | 35.38 | NT | NT |
| Compound No. 61 | 44.89 | NT | NT |
| Compound No. 62 | 40.45 | NT | NT |
| Compound No. 63 | 58.64 | 89.1 ± 1.3 | 2.11 ± 0.11 |
| Compound No. 64 | 60.48 | 95.8 ± 0.7 | 1.39 ± 0.07 |
| Compound No. 67 | 39.24 | NT | NT |
| Compound No. 68 | 31.06 | NT | NT |
| Compound No. 70 | 36.71 | NT | NT |
| Compound No. 71 | 30.74 | NT | NT |
| Compound No. 73 | 41.69 | NT | NT |
| Compound No. 74 | 49.78 | 37.6 ± 0.5 | 14.49 ± 0.68 |
| Compound No. 75 | 33.03 | NT | NT |
| Compound No. 79 | 36.94 | NT | NT |
| Compound No. 82 | 60.78 | 29.10 ± 1.7 | 18.05 ± 0.92 |
| Compound No. 93 | 43.04 | — | 9.55 ± 8.7 |
| Compound No. 94 | 55.99 | — | 6.77 ± 1.45 |
| Compound No. 96 | 41.41 | — | 0.39 ± 0.28 |
| Compound No. 98 | 33.79 | NT | NT |

NT: Not tested

INDUSTRIAL APPLICABILITY

As stated above, the imidazolylalkylcarbonyl derivatives or their pharmaceutically acceptable salts represented by the formula 1 according to the present invention are shown to be excellent T-type calcium channel antagonists, and thus they are expected to be used for the prevention and treatment of cerebral diseases, cardiac diseases and pain-associated diseases.

Accordingly, the compounds of the present invention, by effectively blocking the T-type calcium channel, will be useful for the prevention and treatment of diabetes; cerebral diseases such as epilepsy, Parkinson's disease, dementia; cardiac diseases such as hypertension, cardiac arrhythmia, angina pectoris, myocardial infarction, congestive heart failure; pain-associated diseases such as neuropathic pain, chronic and acute pains.

What is claimed is:

1. Imidazolylalkylcarbonyl derivatives represented by the formula 1 or their pharmaceutically acceptable salts thereof:

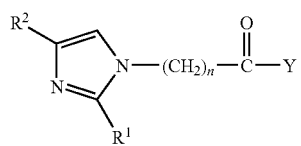

[formula 1]

wherein
Y is

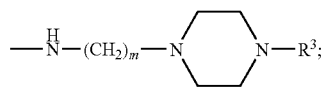

n is an integer of from 2 to 4, m is an integer of from 1 to 4;
$R^1$ and $R^2$, being same or different with each other, are respectively a hydrogen atom, $C_1$-$C_8$ alkyl group, substituted or unsubstituted phenyl group, or substituted or unsubstituted benzyl group; and
$R^3$ is a hydrogen atom, $C_1$-$C_8$ alkyl group, $C_1$-$C_8$ hydroxyalkyl group, CH(substituted or unsubstituted phenyl)$_2$, substituted or unsubstituted phenyl group, or substituted or unsubstituted benzyl group;
wherein said substituted phenyl or benzyl is respectively substituted with a substituent selected from the group consisting of halo, hydroxy, carboxy, alkoxycarbonyl, nitro, amino, mercapto, $C_1$-$C_8$ alkyl, and $C_1$-$C_8$ alkoxy groups.

2. The imidazolylalkylcarbonyl derivatives according to claim 1, wherein
said Y is

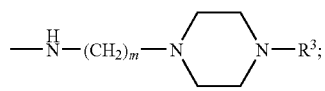

said n is an integer of from 2 to 4, m is an integer of from 1 to 4;
said $R^1$ and $R^2$ are respectively a hydrogen atom, $C_1$-$C_8$ alkyl group, or substituted or unsubstituted phenyl group; and
said $R^3$ is a hydrogen atom, $C_1$-$C_8$ alkyl group, $C_1$-$C_8$ hydroxyalkyl group, CH(substituted or unsubstituted phenyl)$_2$, substituted or unsubstituted phenyl group, or substituted or unsubstituted benzyl group; and
wherein said substituted phenyl or benzyl is respectively substituted with 1-3 substituents selected from the group consisting of halo, $C_1$-$C_8$ alkyl, $C_1$-$C_8$ alkoxy groups.

3. The imidazolylalkylcarbonyl derivatives according to claim 2,
said Y is

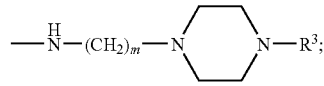

m and n respectively represent an integer of 2 or 3;
said $R^1$ and $R^2$ respectively are a hydrogen atom, methyl, ethyl, propyl, isopropyl, butyl, isobutyl, t-butyl, or phenyl group;
said $R^3$ is methyl, ethyl, propyl, isopropyl, butyl, isobutyl, t-butyl, phenyl, 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methylphenyl, 3-methylphenyl, 4-methylphenyl, 2,3-dimethylphenyl, 2,4-dimethylphenyl, 3,4-dimethylphenyl, 2-methoxyphenyl, 3-methoxyphenyl, 4-methoxyphenyl, 2,3-dimethoxyphenyl, 2,4-dimethoxyphenyl, 3,4-dimethoxyphenyl, benzyl, 2-fluorobenzyl, 3-fluorobenzyl, 4-fluorobenzyl, 2,3-difluorobenzyl, 2,4-difluorobenzyl, 3,4-difluorobenzyl, 2-chlorobenzyl, 3-chlorobenzyl, 4-chlorobenzyl, 2,3-dichlorobenzyl, 2,4-dichlorobenzyl, 3,4-dichlorobenzyl, 2-methylbenzyl, 3-methylbenzyl, 4-methylbenzyl, 2,3-dimethylbenzyl, 2,4-dimethylbenzyl, 3,4-dimethylbenzyl, 2-methoxybenzyl, 3-methoxybenzyl, 4-methoxybenzyl, 2,3-dimethoxybenzyl, 2,4-dimethoxybenzyl, 3,4-dimethoxybenzyl, diphenylmethyl, 2-fluorophenyl(phenyl)methyl, 3-fluorophenyl(phenyl)methyl, 4-fluorophenyl(phenyl)methyl, 2,3-difluorophenyl(phenyl)methyl, 2,4-difluorophenyl(phenyl)methyl, 3,4-difluorophenyl(phenyl)methyl, 2-chlorophenyl(phenyl)methyl, 3-chlorophenyl(phenyl)methyl, 4-chlorophenyl(phenyl)methyl, 2,3-dichlorophenyl(phenyl)methyl, 2,4-dichlorophenyl(phenyl)methyl, 3,4-dichlorophenyl(phenyl)methyl, 2-methylphenyl(phenyl)methyl, 3-methylphenyl(phenyl)methyl, 4-methylphenyl(phenyl)methyl, 2,3-dimethylphenyl(phenyl)methyl, 2,4-dimethylphenyl(phenyl)methyl, 3,4-dimethylphenyl(phenyl)methyl, 2-methoxyphenyl(phenyl)methyl, 3-methoxyphenyl(phenyl)methyl, 4-methoxyphenyl(phenyl)methyl, 2,3-dimethoxyphenyl(phenyl)methyl, 2,4-dimethoxyphenyl(phenyl)methyl, 3,4-dimethoxyphenyl(phenyl)methyl, bis(2-fluorophenyl)methyl, bis(3-fluorophenyl)methyl, bis(4-fluorophenyl)methyl, bis(2,3-difluorophenyl)methyl, bis(2,4-difluorophenyl)methyl, bis(3,4-difluorophenyl)methyl, bis(2-chlorophenyl)methyl, bis(3-chlorophenyl)methyl, bis(4-chlorophenyl)methyl, bis(2,3-dichlorophenyl)methyl, bis(2,4-dichlorophenyl)methyl, bis(3,4-dichlorophenyl)methyl, bis(2-methylphenyl)methyl, bis(3-methylphenyl)methyl, bis(4-methylphenyl)methyl, bis(2,3-dimethylphenyl)methyl, bis(2,4-dimethylphenyl)methyl, bis(3,4-dimethylphenyl)methyl, bis(2-methoxyphenyl)methyl, bis(3-methoxyphenyl)methyl, bis(4-methoxyphenyl)methyl, bis(2,3-dimethoxyphenyl)methyl, bis(2,4-dimethoxyphenyl)methyl, or bis(3,4-dimethoxyphenyl)methyl group.

4. The imidazolylalkylcarbonyl derivatives according to claim 1 selected from the group consisting of:

1-N-[2-(4-diphenylmethylpiperazin-1-yl)ethyl]carbamoylethyl-4-phenylimidazole
1-N-{2-[4-(2,3-dimethylphenyl)(phenyl)methylpiperazin-1-yl]ethyl}carbamoylethyl-4-phenylimidazole
1-N-{2-[4-(3-chlorobenzyl)piperazin-1-yl]ethyl}carbamoylethyl-4-phenylimidazole
1-N-{2-[4-(3,4-dichlorobenzyl)piperazin-1-yl]ethyl}carbamoylethyl-4-phenylimidazole
1-N-{2-[4-(3,4-dichlorobenzyl)piperazin-1-yl]ethyl}carbamoylethyl-2-phenylimidazole
1-N-{2-[4-(3-chlorobenzyl)piperazin-1-yl]ethyl}carbamoylethyl-2-phenylimidazole
1-N-{2-[4-(2,4-dimethylphenyl)piperazin-1-yl]ethyl}carbamoylethyl-4-phenylimidazole
1-N-{2-[4-(2,4-dimethylphenyl)piperazin-1-yl]ethyl}carbamoylethyl-2-phenylimidazole
1-N-{2-[4-(4-chlorophenyl)(phenyl)methylpiperazin-1-yl]ethyl}carbamoylethyl-2-phenylimidazole
1-N-{2-[4-(4-chlorophenyl)(phenyl)methylpiperazin-1-yl]ethyl}carbamoylethyl-4-phenylimidazole
1-N-{2-[4-(2-fluorobenzyl)piperazin-1-yl]ethyl}carbamoylethyl-2-phenylimidazole
1-N-{2-[4-(2-fluorobenzyl)piperazin-1-yl]ethyl}carbamoylethyl-4-phenylimidazole
1-N-{2-[4-(3-methylbenzyl)piperazin-1-yl]ethyl}carbamoylethyl-4-phenylimidazole
1-N-{2-[4-(3-methylbenzyl)piperazin-1-yl]ethyl}carbamoylethyl-2-phenylimidazole
1-N-{2-[4-(4-fluorobenzyl)piperazin-1-yl]ethyl}carbamoylethyl-2-phenylimidazole
1-N-{2-[4-(4-fluorobenzyl)piperazin-1-yl]ethyl}carbamoylethyl-4-phenylimidazole
1-N-[2-(4-phenylpiperazin-1-yl)ethyl]carbamoylethyl-4-phenylimidazole
1-N-[2-(4-phenylpiperazin-1-yl)ethyl]carbamoylethyl-2-phenylimidazole
1-N-{2-[4-(4-fluorophenyl)piperazin-1-yl]ethyl}carbamoylethyl-4-phenylimidazole
1-N-{2-[4-(4-fluorophenyl)piperazin-1-yl]ethyl}carbamoylethyl-2-phenylimidazole
1-N-{2-[4-(4-methoxyphenyl)piperazin-1-yl]ethyl}carbamoylethyl-4-phenylimidazole
1-N-{2-[4-(4-methoxyphenyl)piperazin-1-yl]ethyl}carbamoylethyl-2-phenylimidazole
1-N-{2-[4-(2-fluorophenyl)piperazin-1-yl]ethyl}carbamoylethyl-4-phenylimidazole
1-N-{2-[4-(2-fluorophenyl)piperazin-1-yl]ethyl}carbamoylethyl-2-phenylimidazole
1-N-{2-[4-(3-chlorophenyl)piperazin-1-yl]ethyl}carbamoylethyl-4-phenylimidazole
1-N-{2-[4-(3-chlorophenyl)piperazin-1-yl]ethyl}carbamoylethyl-2-phenylimidazole
1-N-{2-[4-(2,3-dimethylphenyl)piperazin-1-yl]ethyl}carbamoylethyl-2-phenylimidazole
1-N-[2-(4-diphenylmethylpiperazin-1-yl)ethyl]carbamoylethyl-4-phenylimidazole
1-N-[2-(4-benzylpiperazin-1-yl)ethyl]carbamoylethyl-2-phenylimidazole
1-N-[2-(4-benzylpiperazin-1-yl)ethyl]carbamoylethyl-4-phenylimidazole
1-N-[2-(4-phenylpiperazin-1-yl)ethyl]carbamoylethyl-2-methylimidazole
1-N-[2-(4-phenylpiperazin-1-yl)ethyl]carbamoylethyl-4-methylimidazole
1-N-{2-[4-(4-fluorophenyl)piperazin-1-yl]ethyl}carbamoylethyl-4-methylimidazole
1-N-{2-[4-(4-fluorophenyl)piperazin-1-yl]ethyl}carbamoylethyl-2-methylimidazole
1-N-{2-[4-(4-fluorobenzyl)piperazin-1-yl]ethyl}carbamoylethyl-2-methylimidazole
1-N-{2-[4-(4-fluorobenzyl)piperazin-1-yl]ethyl}carbamoylethyl-4-methylimidazole
1-N-{2-[4-(2-fluorophenyl)piperazin-1-yl]ethyl}carbamoylethyl-2-methylimidazole
1-N-{2-[4-(2-fluorophenyl)piperazin-1-yl]ethyl}carbamoylethyl-4-methylimidazole
1-N-{2-[4-(4-chlorophenyl)(phenyl)methylpiperazin-1-yl]ethyl}carbamoylethyl-2-methylimidazole
1-N-{2-[4-(4-chlorophenyl)(phenyl)methylpiperazin-1-yl]ethyl}carbamoylethyl-4-methylimidazole
1-N-{2-[4-benzylpiperazin-1-yl]ethyl}carbamoylethyl-4-methylimidazole
1-N-[2-(4-diphenylmethylpiperazin-1-yl)ethyl]carbamoylethyl-2-methylimidazole
1-N-{2-[4-(4-methoxybenzyl)piperazin-1-yl]ethyl}carbamoylethyl-4-methylimidazole
1-N-{2-[4-(4-methoxybenzyl)piperazin-1-yl]ethyl}carbamoylethyl-2-methylimidazole
1-N-{2-[4-(3,4-dichlorobenzyl)piperazin-1-yl]ethyl}carbamoylethyl-2-methylimidazole
1-N-{2-[4-(3,4-dichlorobenzyl)piperazin-1-yl]ethyl}carbamoylethyl-4-methylimidazole
1-N-{2-[4-(4-chlorobenzyl)piperazin-1-yl]ethyl}carbamoylethyl-2-methylimidazole
1-N-{2-[4-(4-chlorobenzyl)piperazin-1-yl]ethyl}carbamoylethyl-4-methylimidazole
1-N-{2-[4-(3-chlorophenyl)piperazin-1-yl]ethyl}carbamoylethyl-2-methylimidazole
1-N-{2-[4-(3-chlorophenyl)piperazin-1-yl]ethyl}carbamoylethyl-4-methylimidazole and 1-N-{2-[4-diphenylmethylpiperazin-1-yl]ethyl}carbamoylethyl-4-methylimidazole.

5. A pharmaceutical composition comprising imidazolylalkylcarbonyl derivatives or their pharmaceutically acceptable salts according to claim 1 as an active ingredient for the prevention or treatment of diabetes, cerebral diseases, cardiac diseases and pain-associated diseases due to their antagonistic action against T-type calcium channel; diabetes, epilepsy, Parkinson's disease, or dementia; hypertension, cardiac arrhythmia, angina pectoris, myocardial infarction, congestive heart failure; neuropathic pains, chronic pains, or acute pains.

* * * * *